US010349857B2

(12) United States Patent
Grunwald

(10) Patent No.: US 10,349,857 B2
(45) Date of Patent: Jul. 16, 2019

(54) DEVICES AND METHODS FOR ENDOVASCULAR ELECTROGRAPHY

(71) Applicant: Bard Access Systems, Inc., Salt Lake City, UT (US)

(72) Inventor: Sorin Grunwald, Bucharest (RO)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 15/266,977

(22) Filed: Sep. 15, 2016

(65) Prior Publication Data

US 2017/0000367 A1    Jan. 5, 2017

Related U.S. Application Data

(60) Division of application No. 12/854,083, filed on Aug. 10, 2010, now Pat. No. 9,445,734, which is a
(Continued)

(51) Int. Cl.
*A61N 1/05*    (2006.01)
*A61B 5/0452*    (2006.01)
(Continued)

(52) U.S. Cl.
CPC .......... *A61B 5/0452* (2013.01); *A61B 5/042* (2013.01); *A61B 5/04017* (2013.01); *A61B 5/06* (2013.01);
(Continued)

(58) Field of Classification Search
CPC ... A61B 5/0006; A61B 5/04017; A61B 5/042; A61B 5/0452; A61B 5/06; A61B 5/061; A61B 5/065; A61B 5/066
See application file for complete search history.

(56) References Cited

U.S. PATENT DOCUMENTS 3,795,855 A    3/1974 Browning
3,817,241 A    6/1974 Grausz
(Continued)

FOREIGN PATENT DOCUMENTS

CN    2031655 U    2/1989
CN    1913833 A    2/2007
(Continued)

OTHER PUBLICATIONS

AU 2012278809 filed Nov. 12, 2013 Notice of Acceptance dated Sep. 13, 2016.
(Continued)

*Primary Examiner* — Tammie K Marlen
(74) *Attorney, Agent, or Firm* — Rutan & Tucker, LLP

(57) ABSTRACT

A method for positioning an endovascular device in or near the heart using electrocardiogram (ECG) signals. The method includes receiving an endovascular ECG signal including a plurality of waveforms, processing the endovascular ECG signal to calculate a P-wave amplitude and a spectral power for each predetermined time period, determining a maximum P-wave amplitude and an associated maximum spectral power, associating the maximum P-wave amplitude and the maximum spectral power with a predetermined location in or near the heart, calculating a location based on a ratio of the P-wave amplitude to the maximum P-wave amplitude and a ratio of the spectral power to the maximum spectral power, and displaying the location to a user.

16 Claims, 17 Drawing Sheets

Related U.S. Application Data continuation-in-part of application No. 12/815,331, filed on Jun. 14, 2010, now Pat. No. 9,339,206.

(60) Provisional application No. 61/213,474, filed on Jun. 12, 2009, provisional application No. 61/272,025, filed on Aug. 10, 2009.

(51) Int. Cl.

| | | |
|---|---|---|
| *A61B 5/04* | (2006.01) | |
| *A61B 5/042* | (2006.01) | |
| *A61B 5/06* | (2006.01) | |
| *A61M 25/00* | (2006.01) | |
| *A61M 25/01* | (2006.01) | |
| *A61B 34/20* | (2016.01) | |
| *A61B 5/00* | (2006.01) | |
| *A61M 25/09* | (2006.01) | |
| *A61M 39/10* | (2006.01) | |

(52) U.S. Cl.
CPC .............. *A61B 5/065* (2013.01); *A61B 5/742* (2013.01); *A61B 34/20* (2016.02); *A61M 25/0026* (2013.01); *A61M 25/0097* (2013.01); *A61M 25/0102* (2013.01); *A61M 25/0147* (2013.01); *A61N 1/056* (2013.01); *A61B 5/7203* (2013.01); *A61B 5/726* (2013.01); *A61M 25/0194* (2013.01); *A61M 2025/09116* (2013.01); *A61M 2039/1022* (2013.01)

(56) References Cited

U.S. PATENT DOCUMENTS

| | | |
|---|---|---|
| 3,902,501 A | 9/1975 | Citron et al. |
| 3,995,623 A | 12/1976 | Blake et al. |
| 4,365,639 A | 12/1982 | Goldreyer |
| 4,565,201 A | 1/1986 | Lass |
| 4,577,634 A | 3/1986 | Gessman |
| 4,587,975 A | 5/1986 | Salo et al. |
| 4,595,012 A | 6/1986 | Webler et al. |
| 4,644,960 A | 2/1987 | Johans |
| 4,681,117 A | 7/1987 | Brodman et al. |
| 4,793,361 A | 12/1988 | DuFault |
| 4,809,681 A | 3/1989 | Kantrowitz et al. |
| 4,821,731 A | 4/1989 | Martinelli et al. |
| 4,836,214 A | 6/1989 | Sramek |
| 4,852,580 A | 8/1989 | Wood |
| 4,873,987 A | 10/1989 | Djordjevich et al. |
| 4,905,698 A | 3/1990 | Strohl, Jr. et al. |
| 4,957,110 A | 9/1990 | Vogel et al. |
| 5,029,585 A | 7/1991 | Lieber et al. |
| 5,058,583 A | 10/1991 | Geddes et al. |
| 5,058,595 A | 10/1991 | Kern |
| 5,092,341 A | 3/1992 | Kelen |
| 5,109,862 A | 5/1992 | Kelen et al. |
| 5,121,750 A | 6/1992 | Katims |
| 5,146,151 A | 9/1992 | Korn |
| 5,184,627 A | 2/1993 | de Toledo |
| 5,220,924 A | 6/1993 | Frazin |
| 5,243,995 A | 9/1993 | Maier |
| 5,269,306 A | 12/1993 | Warnking et al. |
| 5,330,496 A | 7/1994 | Alferness |
| 5,385,146 A | 1/1995 | Goldreyer |
| 5,398,683 A | 3/1995 | Edwards et al. |
| 5,417,701 A | 5/1995 | Holmes |
| 5,450,846 A | 9/1995 | Goldreyer |
| 5,500,011 A | 3/1996 | Desai |
| 5,517,989 A | 5/1996 | Frisbie et al. |
| 5,540,681 A | 7/1996 | Strul et al. |
| 5,570,671 A | 11/1996 | Hickey |
| 5,640,967 A | 6/1997 | Fine et al. |
| 5,718,241 A | 2/1998 | Ben-Haim et al. |
| 5,727,550 A | 3/1998 | Montecalvo |
| 5,730,129 A | 3/1998 | Darrow et al. |
| 5,769,786 A | 6/1998 | Wiegel |
| 5,820,560 A | 10/1998 | Sinderby et al. |
| 5,830,145 A | 11/1998 | Tenhoff |
| 5,833,622 A | 11/1998 | Meathrel et al. |
| 5,840,030 A | 11/1998 | Ferek-Petric et al. |
| 5,840,031 A | 11/1998 | Crowley |
| 5,846,198 A | 12/1998 | Killmann |
| 5,899,860 A | 5/1999 | Pfeiffer et al. |
| 5,908,385 A | 6/1999 | Chechelski et al. |
| 5,931,863 A | 8/1999 | Griffin, III et al. |
| 5,935,160 A | 8/1999 | Auricchio et al. |
| 5,944,022 A | 8/1999 | Nardella et al. |
| 5,951,472 A | 9/1999 | Van Vaals et al. |
| 5,967,978 A | 10/1999 | Littmann et al. |
| 5,983,126 A | 11/1999 | Wittkampf |
| 6,006,123 A | 12/1999 | Nguyen et al. |
| 6,014,473 A | 1/2000 | Hossack et al. |
| 6,019,725 A | 2/2000 | Vesely et al. |
| 6,052,618 A | 4/2000 | Dahlke et al. |
| 6,058,323 A | 5/2000 | Lemelson |
| 6,063,032 A | 5/2000 | Grunwald |
| 6,102,862 A | 8/2000 | Grunwald et al. |
| 6,107,699 A | 8/2000 | Swanson |
| 6,115,624 A | 9/2000 | Lewis et al. |
| 6,190,370 B1 | 2/2001 | Tsui |
| 6,197,001 B1 | 3/2001 | Wilson et al. |
| 6,212,426 B1 | 4/2001 | Swanson |
| 6,217,517 B1 | 4/2001 | Grunwald |
| 6,230,042 B1 | 5/2001 | Slettenmark |
| 6,231,518 B1 | 5/2001 | Grabek et al. |
| 6,236,883 B1 | 5/2001 | Ciaccio et al. |
| 6,246,898 B1 | 6/2001 | Vesely et al. |
| 6,249,234 B1 | 6/2001 | Ely et al. |
| 6,254,543 B1 | 7/2001 | Grunwald et al. |
| 6,259,938 B1 | 7/2001 | Zarychta et al. |
| 6,266,551 B1 | 7/2001 | Osadchy et al. |
| 6,266,552 B1 | 7/2001 | Slettenmark |
| 6,266,563 B1 | 7/2001 | KenKnight et al. |
| 6,275,724 B1 | 8/2001 | Dickinson et al. |
| 6,287,259 B1 | 9/2001 | Grunwald |
| 6,324,416 B1 | 11/2001 | Seibert |
| 6,350,160 B1 | 2/2002 | Feuersanger et al. |
| 6,354,999 B1 | 3/2002 | Dgany et al. |
| 6,360,123 B1 | 3/2002 | Kimchi et al. |
| 6,379,303 B1 | 4/2002 | Seitz et al. |
| 6,385,476 B1 | 5/2002 | Osadchy et al. |
| 6,398,738 B1 | 6/2002 | Millar |
| 6,406,422 B1 | 6/2002 | Landesberg |
| 6,471,656 B1 | 10/2002 | Shalman et al. |
| 6,494,832 B1 | 12/2002 | Feldman et al. |
| 6,508,802 B1 | 1/2003 | Rosengart et al. |
| 6,511,413 B2 | 1/2003 | Landesberg |
| 6,514,202 B2 | 2/2003 | Grunwald |
| 6,514,249 B1 | 2/2003 | Maguire et al. |
| 6,522,906 B1 | 2/2003 | Salisbury, Jr. et al. |
| 6,538,634 B1 | 3/2003 | Chui et al. |
| 6,540,699 B1 | 4/2003 | Smith et al. |
| 6,546,270 B1 | 4/2003 | Goldin et al. |
| 6,569,160 B1 | 5/2003 | Goldin et al. |
| 6,569,862 B1 | 5/2003 | Marban |
| 6,577,896 B2 | 6/2003 | Werner et al. |
| 6,584,343 B1 | 6/2003 | Ransbury et al. |
| 6,589,181 B2 | 7/2003 | Grunwald et al. |
| 6,649,914 B1 | 11/2003 | Moorman et al. |
| 6,690,968 B2 | 2/2004 | Mejia |
| 6,709,390 B1 | 3/2004 | Marie Pop |
| 6,719,756 B1 | 4/2004 | Muntermann |
| 6,733,458 B1 | 5/2004 | Steins et al. |
| 6,763,261 B2 | 7/2004 | Casscells, III et al. |
| 6,816,266 B2 | 11/2004 | Varshneya et al. |
| 6,941,166 B2 | 9/2005 | MacAdam et al. |
| 6,945,938 B2 | 9/2005 | Grunwald |
| 6,950,689 B1 | 9/2005 | Willis et al. |
| 6,959,214 B2 | 10/2005 | Pape et al. |
| 7,015,393 B2 | 3/2006 | Weiner et al. |
| 7,096,059 B2 | 8/2006 | Geddes et al. |
| 7,141,019 B2 | 11/2006 | Pearlman |
| 7,184,820 B2 | 2/2007 | Jersey-Willuhn et al. |
| 7,190,819 B2 | 3/2007 | Viswanathan |

(56) References Cited

U.S. PATENT DOCUMENTS

| | | |
|---|---|---|
| 7,207,941 B2 | 4/2007 | Sharf |
| 7,231,243 B2 | 6/2007 | Tearney et al. |
| 7,261,691 B1 | 8/2007 | Asomani |
| 7,299,085 B2 | 11/2007 | Bergelson et al. |
| 7,308,296 B2 | 12/2007 | Lys et al. |
| 7,327,872 B2 | 2/2008 | Vaillant et al. |
| 7,331,462 B2 | 2/2008 | Steppe |
| 7,366,563 B2 | 4/2008 | Kleen et al. |
| 7,479,141 B2 | 1/2009 | Kleen et al. |
| 7,529,584 B2 | 5/2009 | Laske et al. |
| 7,546,158 B2 | 6/2009 | Allison et al. |
| 7,613,478 B2 | 11/2009 | Jabri et al. |
| 7,640,053 B2 | 12/2009 | Verin |
| 7,666,191 B2 | 2/2010 | Orban, III et al. |
| 7,699,829 B2 | 4/2010 | Harris et al. |
| 7,729,743 B2 | 6/2010 | Sabczynski et al. |
| 7,774,051 B2 | 8/2010 | Voth |
| 7,774,055 B1 | 8/2010 | Min |
| 7,822,464 B2 | 10/2010 | Maschke et al. |
| 7,831,294 B2 | 11/2010 | Viswanathan |
| 7,840,252 B2 | 11/2010 | Strommer et al. |
| 7,846,157 B2 | 12/2010 | Kozel |
| 7,869,854 B2 | 1/2011 | Shachar et al. |
| 7,869,865 B2 | 1/2011 | Govari et al. |
| 7,873,402 B2 | 1/2011 | Shachar |
| 7,947,040 B2 | 5/2011 | Davies et al. |
| 7,969,142 B2 | 6/2011 | Krueger et al. |
| 8,055,327 B2 | 11/2011 | Strommer et al. |
| 8,057,394 B2 | 11/2011 | Dala-Krishna |
| 8,082,025 B2 | 12/2011 | Amitai et al. |
| 8,090,430 B2 | 1/2012 | Makower et al. |
| 8,105,338 B2 | 1/2012 | Anderson et al. |
| 8,155,732 B2 | 4/2012 | Scholz et al. |
| 8,241,274 B2 | 8/2012 | Keogh et al. |
| 8,244,339 B2 | 8/2012 | Shen et al. |
| 8,255,035 B2 | 8/2012 | Cao et al. |
| 8,303,505 B2 | 11/2012 | Webler et al. |
| 8,326,419 B2 | 12/2012 | Rosenberg et al. |
| 8,326,651 B2 | 12/2012 | McLaren et al. |
| 8,346,343 B2 | 1/2013 | Kimura et al. |
| 8,369,922 B2 | 2/2013 | Paul et al. |
| 8,388,541 B2 | 3/2013 | Messerly et al. |
| 8,391,956 B2 | 3/2013 | Zellers et al. |
| 8,400,164 B2 | 3/2013 | Osadchy et al. |
| 8,401,616 B2 | 3/2013 | Verard et al. |
| 8,412,313 B2 | 4/2013 | Amitai et al. |
| 8,456,182 B2 | 6/2013 | Bar-Tal et al. |
| 8,478,388 B2 | 7/2013 | Nguyen et al. |
| 8,494,608 B2 | 7/2013 | Markowitz et al. |
| 8,504,139 B2 | 8/2013 | Jacobsen et al. |
| 8,521,122 B2 | 8/2013 | Scott et al. |
| 8,527,036 B2 | 9/2013 | Jalde et al. |
| 8,538,509 B2 | 9/2013 | Harlev et al. |
| 8,597,193 B2 | 12/2013 | Grunwald et al. |
| 8,620,412 B2 | 12/2013 | Griffiths et al. |
| 8,644,907 B2 | 2/2014 | Hartmann et al. |
| 8,663,116 B2 | 3/2014 | Hamilton, Jr. |
| 8,690,776 B2 | 4/2014 | Razzaque et al. |
| 8,700,137 B2 | 4/2014 | Albert |
| 8,715,195 B2 | 5/2014 | Ziv |
| 8,721,655 B2 | 5/2014 | Viswanathan et al. |
| 8,761,862 B2 | 6/2014 | Ridley et al. |
| 8,942,784 B2 | 1/2015 | Neidert et al. |
| 8,965,490 B2 | 2/2015 | Lee et al. |
| 8,971,994 B2 | 3/2015 | Burnside et al. |
| 9,014,794 B2 | 4/2015 | Brodnick et al. |
| 9,033,889 B2 | 5/2015 | Hamilton, Jr. |
| 9,179,860 B2 | 11/2015 | Markowitz et al. |
| 9,198,600 B2 | 12/2015 | Grunwald et al. |
| 9,415,188 B2 | 8/2016 | He et al. |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,526,440 B2 | 12/2016 | Burnside et al. |
| 9,532,724 B2 | 1/2017 | Grunwald |
| 9,554,716 B2 | 1/2017 | Burnside et al. |
| 9,636,031 B2 | 5/2017 | Cox |
| 9,642,986 B2 | 5/2017 | Beasley |
| 9,649,048 B2 | 5/2017 | Cox et al. |
| 9,681,823 B2 | 6/2017 | Messerly et al. |
| 9,833,169 B2 | 12/2017 | Rothenberg |
| 9,839,372 B2 | 12/2017 | Bukhman et al. |
| 9,901,714 B2 | 2/2018 | Lemon et al. |
| 9,907,513 B2 | 3/2018 | Silverstein |
| 9,999,371 B2 | 6/2018 | Messerly et al. |
| 10,004,875 B2 | 6/2018 | Bown et al. |
| 10,046,139 B2 | 8/2018 | Powers et al. |
| 10,105,121 B2 | 10/2018 | Burnside et al. |
| 10,165,962 B2 | 1/2019 | Messerly et al. |
| 10,231,643 B2 | 3/2019 | Grunwald |
| 10,231,753 B2 | 3/2019 | Burnside et al. |
| 10,238,418 B2 | 3/2019 | Cox et al. |
| 10,271,762 B2 | 4/2019 | Grunwald |
| 2001/0014774 A1 | 8/2001 | Grunwald |
| 2001/0027332 A1 | 10/2001 | Grunwald et al. |
| 2002/0173721 A1 | 11/2002 | Grunwald et al. |
| 2002/0193756 A1 | 12/2002 | Prindle |
| 2003/0009132 A1 | 1/2003 | Schwartz et al. |
| 2003/0013959 A1 | 1/2003 | Grunwald et al. |
| 2003/0018251 A1 | 1/2003 | Solomon |
| 2003/0036696 A1 | 2/2003 | Willis et al. |
| 2003/0083698 A1 | 5/2003 | Whitehurst et al. |
| 2003/0092993 A1 | 5/2003 | Grunwald |
| 2003/0149368 A1 | 8/2003 | Hennemann et al. |
| 2003/0162414 A1 | 8/2003 | Schulz et al. |
| 2003/0220578 A1 | 11/2003 | Ho et al. |
| 2003/0236445 A1 | 12/2003 | Couvillon |
| 2004/0059217 A1 | 3/2004 | Kessman et al. |
| 2004/0059237 A1 | 3/2004 | Narayan et al. |
| 2004/0138569 A1 | 7/2004 | Grunwald et al. |
| 2004/0150963 A1 | 8/2004 | Holmberg et al. |
| 2004/0243118 A1 | 12/2004 | Ayers et al. |
| 2004/0267086 A1 | 12/2004 | Anstadt et al. |
| 2005/0085715 A1 | 4/2005 | Dukesherer et al. |
| 2005/0178396 A1 | 8/2005 | Hunter et al. |
| 2005/0182454 A1 | 8/2005 | Gharib et al. |
| 2005/0256398 A1 | 11/2005 | Hastings et al. |
| 2005/0283210 A1 | 12/2005 | Blischak et al. |
| 2005/0283216 A1 | 12/2005 | Pyles |
| 2006/0217755 A1 | 9/2006 | Eversull et al. |
| 2006/0241432 A1 | 10/2006 | Herline et al. |
| 2006/0253029 A1 | 11/2006 | Altmann et al. |
| 2006/0253115 A1 | 11/2006 | Avitall et al. |
| 2006/0287595 A1 | 12/2006 | Maschke |
| 2007/0010753 A1 | 1/2007 | MacAdam |
| 2007/0016007 A1 | 1/2007 | Govari et al. |
| 2007/0016013 A1 | 1/2007 | Camus |
| 2007/0049817 A1 | 3/2007 | Preiss et al. |
| 2007/0049846 A1 | 3/2007 | Bown et al. |
| 2007/0055141 A1 | 3/2007 | Kruger et al. |
| 2007/0055142 A1 | 3/2007 | Webler |
| 2007/0055294 A1 | 3/2007 | Giap |
| 2007/0060992 A1 | 3/2007 | Pappone |
| 2007/0066888 A1 | 3/2007 | Maschke |
| 2007/0078343 A1 | 4/2007 | Kawashima et al. |
| 2007/0093710 A1 | 4/2007 | Maschke |
| 2007/0135803 A1 | 6/2007 | Belson |
| 2007/0135886 A1 | 6/2007 | Maschke |
| 2007/0161914 A1 | 7/2007 | Zdeblick et al. |
| 2007/0161915 A1 | 7/2007 | Desai |
| 2007/0167738 A1 | 7/2007 | Timinger et al. |
| 2007/0197905 A1 | 8/2007 | Timinger et al. |
| 2007/0197926 A1 | 8/2007 | Danehorn et al. |
| 2007/0225589 A1 | 9/2007 | Viswanathan |
| 2007/0225610 A1 | 9/2007 | Mickley et al. |
| 2007/0232882 A1 | 10/2007 | Glossop et al. |
| 2007/0232896 A1 | 10/2007 | Gilboa et al. |
| 2007/0239004 A1 | 10/2007 | Kakee et al. |
| 2007/0247454 A1 | 10/2007 | Rahn et al. |
| 2007/0299353 A1 | 12/2007 | Harley et al. |
| 2008/0033282 A1 | 2/2008 | Bar-Tal et al. |
| 2008/0081958 A1 | 4/2008 | Denison et al. |
| 2008/0082136 A1 | 4/2008 | Gaudiani |
| 2008/0108949 A1 | 5/2008 | Beasley et al. |

(56) References Cited

U.S. PATENT DOCUMENTS

| | | |
|---|---|---|
| 2008/0119697 A1 | 5/2008 | Vadodaria et al. |
| 2008/0137927 A1 | 6/2008 | Altmann et al. |
| 2008/0146939 A1 | 6/2008 | McMorrow et al. |
| 2008/0146940 A1 | 6/2008 | Jenkins et al. |
| 2008/0146941 A1 | 6/2008 | Dala-Krishna |
| 2008/0146942 A1 | 6/2008 | Dala-Krishna |
| 2008/0190438 A1 | 8/2008 | Harlev et al. |
| 2008/0200801 A1 | 8/2008 | Wildes et al. |
| 2008/0200913 A1 | 8/2008 | Viswanathan |
| 2008/0269581 A1 | 10/2008 | Wood et al. |
| 2009/0062646 A1 | 3/2009 | Creighton, IV et al. |
| 2009/0062772 A1 | 3/2009 | Wakeford et al. |
| 2009/0080738 A1 | 3/2009 | Zur et al. |
| 2009/0099468 A1 | 4/2009 | Thiagalingam et al. |
| 2009/0115406 A1 | 5/2009 | Anderson et al. |
| 2009/0204113 A1 | 8/2009 | MacAdam et al. |
| 2009/0209872 A1 | 8/2009 | Pop |
| 2009/0209950 A1 | 8/2009 | Starksen |
| 2009/0270729 A1 | 10/2009 | Corbucci et al. |
| 2009/0270746 A1 | 10/2009 | Min |
| 2009/0281419 A1 | 11/2009 | Troesken et al. |
| 2009/0312629 A1 | 12/2009 | Razzaque et al. |
| 2010/0004547 A1 | 1/2010 | Scholz et al. |
| 2010/0041973 A1 | 2/2010 | Vu et al. |
| 2010/0049062 A1 | 2/2010 | Ziv |
| 2010/0076328 A1 | 3/2010 | Matsumura et al. |
| 2010/0106011 A1 | 4/2010 | Byrd et al. |
| 2010/0113917 A1 | 5/2010 | Anderson |
| 2010/0117659 A1 | 5/2010 | Osadchy et al. |
| 2010/0130858 A1 | 5/2010 | Arai et al. |
| 2010/0152596 A1 | 6/2010 | Griffiths et al. |
| 2010/0152604 A1 | 6/2010 | Kaula et al. |
| 2010/0160772 A1 | 6/2010 | Gardeski et al. |
| 2010/0204614 A1 | 8/2010 | Lindquist et al. |
| 2010/0217116 A1 | 8/2010 | Eck et al. |
| 2010/0274150 A1 | 10/2010 | Harley et al. |
| 2010/0291521 A1 | 11/2010 | Simon |
| 2011/0015496 A1 | 1/2011 | Sherman et al. |
| 2011/0106101 A1 | 5/2011 | Tortonese et al. |
| 2011/0282187 A1 | 11/2011 | Harlev et al. |
| 2011/0282285 A1 | 11/2011 | Blanchard et al. |
| 2011/0282686 A1 | 11/2011 | Venon et al. |
| 2011/0295108 A1 | 12/2011 | Cox et al. |
| 2011/0306859 A1 | 12/2011 | Saldivar et al. |
| 2012/0004564 A1 | 1/2012 | Dobak, III |
| 2012/0059270 A1 | 3/2012 | Grunwald |
| 2012/0059271 A1 | 3/2012 | Amitai et al. |
| 2012/0071751 A1 | 3/2012 | Sra et al. |
| 2012/0071782 A1 | 3/2012 | Patil et al. |
| 2012/0095319 A1 | 4/2012 | Kondrosky et al. |
| 2012/0143029 A1 | 6/2012 | Silverstein et al. |
| 2012/0265084 A1 | 10/2012 | Stewart et al. |
| 2012/0296200 A1 | 11/2012 | Shachar et al. |
| 2012/0310052 A1 | 12/2012 | Mahapatra et al. |
| 2012/0310066 A1 | 12/2012 | Shachar et al. |
| 2012/0310660 A1 | 12/2012 | Liu et al. |
| 2013/0006100 A1 | 1/2013 | Shachar et al. |
| 2013/0018248 A1 | 1/2013 | Hurezan |
| 2013/0041254 A1 | 2/2013 | Hagy et al. |
| 2013/0079628 A1 | 3/2013 | Groszmann et al. |
| 2013/0085416 A1 | 4/2013 | Mest |
| 2013/0090938 A1 | 4/2013 | Fishman et al. |
| 2013/0131503 A1 | 5/2013 | Schneider et al. |
| 2013/0169272 A1 | 7/2013 | Eichler et al. |
| 2013/0281837 A1 | 10/2013 | Ridley et al. |
| 2013/0289417 A1 | 10/2013 | Grunwald et al. |
| 2013/0296693 A1 | 11/2013 | Wenzel et al. |
| 2013/0303878 A1 | 11/2013 | Nevo et al. |
| 2013/0303945 A1 | 11/2013 | Blumenkranz et al. |
| 2013/0345555 A1 | 12/2013 | Kanade et al. |
| 2014/0089836 A1 | 3/2014 | Damani et al. |
| 2014/0128712 A1 | 5/2014 | Banet et al. |
| 2014/0187917 A1 | 7/2014 | Clark et al. |
| 2014/0187990 A1 | 7/2014 | Banet et al. |
| 2014/0221862 A1 | 8/2014 | Tambe |
| 2014/0249428 A1 | 9/2014 | Ingold, Jr. et al. |
| 2014/0249505 A1 | 9/2014 | Bukhman |
| 2014/0253270 A1 | 9/2014 | Nicholls et al. |
| 2014/0257080 A1 | 9/2014 | Dunbar et al. |
| 2014/0276010 A1 | 9/2014 | Anderson |
| 2015/0025365 A1 | 1/2015 | Esguerra Wilczynski et al. |
| 2015/0025402 A1 | 1/2015 | Rothenberg |
| 2015/0073285 A1 | 3/2015 | Albert et al. |
| 2015/0080716 A1 | 3/2015 | Powers et al. |
| 2015/0209008 A1 | 7/2015 | Ridley et al. |
| 2015/0216445 A1 | 8/2015 | Carmeli et al. |
| 2015/0216446 A1 | 8/2015 | Bukhman et al. |
| 2015/0223775 A1 | 8/2015 | Hamilton, Jr. |
| 2015/0245809 A1 | 9/2015 | Hagy et al. |
| 2015/0245872 A1 | 9/2015 | Hagy et al. |
| 2015/0246247 A1 | 9/2015 | Binnekamp et al. |
| 2015/0282734 A1 | 10/2015 | Schweikert et al. |
| 2015/0289781 A1 | 10/2015 | Grunwald et al. |
| 2015/0317810 A1 | 11/2015 | Grunwald et al. |
| 2015/0335310 A1 | 11/2015 | Bernstein et al. |
| 2015/0335383 A9 | 11/2015 | Cohen |
| 2016/0067449 A1 | 3/2016 | Misener et al. |
| 2016/0278869 A1 | 9/2016 | Grunwald |
| 2016/0374589 A1 | 12/2016 | Misener et al. |
| 2017/0020561 A1 | 1/2017 | Cox et al. |
| 2017/0079548 A1 | 3/2017 | Silverstein et al. |
| 2017/0079552 A1 | 3/2017 | Grunwald |
| 2017/0079615 A1 | 3/2017 | Burnside et al. |
| 2017/0079681 A1 | 3/2017 | Burnside et al. |
| 2017/0086782 A1 | 3/2017 | Hagy et al. |
| 2017/0151022 A1 | 6/2017 | Jascob et al. |
| 2017/0215762 A1 | 8/2017 | Burnside et al. |
| 2017/0231700 A1 | 8/2017 | Cox et al. |
| 2017/0281029 A1 | 10/2017 | Messerly et al. |
| 2018/0070856 A1 | 3/2018 | Grunwald |
| 2018/0103869 A1 | 4/2018 | Bukhman et al. |
| 2018/0116551 A1 | 5/2018 | Newman et al. |
| 2018/0169389 A1 | 6/2018 | Lemon et al. |
| 2019/0069877 A1 | 3/2019 | Burnside et al. |
| 2019/0099108 A1 | 4/2019 | Messerly et al. |

FOREIGN PATENT DOCUMENTS

| | | |
|---|---|---|
| CN | 101854853 A | 10/2010 |
| DE | 1319033 C1 | 6/1994 |
| EP | 0359697 | 3/1990 |
| EP | 0362821 | 4/1990 |
| EP | 1015967 B1 | 4/2002 |
| EP | 1504713 A1 | 2/2005 |
| EP | 1117331 B1 | 5/2005 |
| EP | 1117332 B1 | 8/2005 |
| EP | 1118019 B1 | 5/2006 |
| EP | 1717601 A2 | 11/2006 |
| EP | 1887940 A2 | 2/2008 |
| EP | 2531098 A1 | 12/2012 |
| EP | 2605699 A2 | 6/2013 |
| EP | 2474268 B1 | 7/2013 |
| EP | 2618727 A1 | 7/2013 |
| EP | 2992825 B1 | 5/2017 |
| EP | 2170162 B1 | 8/2017 |
| EP | 2265175 B1 | 8/2017 |
| JP | 2001-145630 A | 5/2001 |
| JP | 2002-224069 A | 8/2002 |
| JP | 2007-105450 A | 4/2007 |
| JP | 2007-313122 A | 12/2007 |
| RU | 2009101949 A | 7/2010 |
| WO | 1980002376 A1 | 11/1980 |
| WO | 1997/22395 A1 | 6/1997 |
| WO | 97/48438 A2 | 12/1997 |
| WO | 1998035611 A1 | 8/1998 |
| WO | 1999049407 A1 | 9/1999 |
| WO | 2000074775 A1 | 12/2000 |
| WO | 2001013792 A1 | 3/2001 |
| WO | 02/07794 A2 | 1/2002 |
| WO | 2003077759 A1 | 9/2003 |
| WO | 2004002303 A1 | 1/2004 |
| WO | 2005/089851 A1 | 9/2005 |
| WO | 2005117690 A1 | 12/2005 |
| WO | 2005117733 A2 | 12/2005 |

(56) References Cited

FOREIGN PATENT DOCUMENTS

| WO | 2007002541 A2 | 1/2007 |
|---|---|---|
| WO | 2007005976 A1 | 1/2007 |
| WO | 2007067324 A1 | 6/2007 |
| WO | 2007069168 A2 | 6/2007 |
| WO | 2007109123 A2 | 9/2007 |
| WO | 2007126536 A2 | 11/2007 |
| WO | 2008097767 A2 | 8/2008 |
| WO | 2008118992 A1 | 10/2008 |
| WO | 2008126074 A2 | 10/2008 |
| WO | 2008129326 A1 | 10/2008 |
| WO | 2008131017 A2 | 10/2008 |
| WO | 2008136008 A2 | 11/2008 |
| WO | 2009003138 A1 | 12/2008 |
| WO | 2009100158 A1 | 8/2009 |
| WO | 2009123819 A2 | 10/2009 |
| WO | 2009126340 A1 | 10/2009 |
| WO | 2009129477 A1 | 10/2009 |
| WO | 2009134605 A2 | 11/2009 |
| WO | 2010018500 A1 | 2/2010 |
| WO | 2011057289 A2 | 5/2011 |
| WO | 2012039866 A1 | 3/2012 |
| WO | 2012173697 A1 | 12/2012 |
| WO | 2014042329 A1 | 3/2014 |
| WO | 2015/055797 A1 | 4/2015 |
| WO | 2015048514 A1 | 4/2015 |
| WO | 2015073962 A1 | 5/2015 |
| WO | 2015/120256 A2 | 8/2015 |
| WO | 2016/210325 A1 | 12/2016 |
| WO | 2018/112252 A1 | 6/2018 |

OTHER PUBLICATIONS

CA 2,721,715 filed Apr. 17, 2009 Examiner's Report dated Oct. 25, 2016.
CA 2800810 filed Nov. 26, 2012 Office Action dated Mar. 30, 2017.
CN 200980144663.8 filed May 9, 2011 Decision of Re-Examination dated Feb. 21, 2017.
CN 200980144663.8 filed May 9, 2011 Notice of Reexamination dated Aug. 5, 2016.
CN 201180037065.8 filed Jan. 28, 2013 Notice of Grant dated Aug. 30, 2016.
CN 201380051172.5 filed Mar. 30, 2015 Office Action dated May 2, 2017.
CN 201380065663.5 filed Jun. 15, 2015 Office Action dated Mar. 15, 2017.
CN 201510144728.6 filed Apr. 17, 2015 Office Action dated Jan. 23, 2017.
CO 15110530 filed May 14, 2015 Office Action dated May 8, 2017.
CO 15110530 filed May 14, 2015 Office Action dated Nov. 25, 2016.
EP 09743249.6 filed Oct. 18, 2010 Intention to Grant dated Mar. 2, 2017.
EP 11850625.2 filed Jul. 22, 2013 Extended European Search Report dated Jun. 21, 2017.
EP 13840356.3 filed Apr. 27, 2015 Extended European Search Report dated Mar. 22, 2017.
EP 13840356.3 filed Apr. 27, 2015 Partial European Search Report dated Oct. 19, 2016.
EP 13846380.7 filed May 15, 2015 Extended European Search Report dated Sep. 30, 2016.
EP 13846380.7 filed May 15, 2015 Partial European Search Report dated Sep. 30, 2016.
EP 14761249.3 Filed Sep. 3, 2015 Extended European Search Report dated Sep. 19, 2016.
EP 15746326.6 filed Jul. 1, 2016 Extended European Search Report dated Jun. 9, 2017.
EP 17157118.5 filed Feb. 21, 2017 Extended European Search Report Jun. 8, 2017.
JP 2013-530322 filed Mar. 18, 2013, Office Action dated Mar. 2, 2017.
JP 2015-534770 filed Mar. 26, 2015 Office Action dated Jun. 12, 2017.
KR 10-2012-7000866 filed Jan. 11, 2012 Second Office Action dated Nov. 3, 2016.
PCT/US2016/039356 filed Jun. 24, 2016 International Search Report and Written Opinion dated Sep. 16, 2016.
U.S. Appl. No. 12/426,175, filed Apr. 17, 2009 Decision on Appeal dated Nov. 7, 2016.
U.S. Appl. No. 12/426,175, filed Apr. 17, 2009 Notice of Allowance dated Dec. 13, 2016.
U.S. Appl. No. 12/545,762, filed Aug. 21, 2009 Final Office Action dated Apr. 10, 2017.
U.S. Appl. No. 12/545,762, filed Aug. 21, 2009 Non-Final Office Action dated Sep. 26, 2016.
U.S. Appl. No. 12/545,762, filed Aug. 21, 2009 Notice of Panel Decision dated Jul. 14, 2017.
U.S. Appl. No. 12/893,916, filed Sep. 29, 2010 Non-Final Office Action dated Aug. 31, 2016.
U.S. Appl. No. 13/118,033, filed May 27, 2011 Notice of Allowance dated Sep. 2, 2016.
U.S. Appl. No. 13/469,932, filed May 11, 2012 Notice of Allowance dated Jan. 31, 2017.
U.S. Appl. No. 13/665,420, filed Oct. 31, 2012 Non-Final Office Action dated Mar. 15, 2017.
U.S. Appl. No. 13/890,158, filed May 8, 2013 Non-Final Office Action dated Apr. 7, 2017.
U.S. Appl. No. 14/040,205, filed Sep. 27, 2013 Advisory Action dated Dec. 15, 2016.
U.S. Appl. No. 14/040,205, filed Sep. 27, 2013 Examiner's Answer dated Jul. 20, 2017.
U.S. Appl. No. 14/040,205, filed Sep. 27, 2013 Final Office Action dated Oct. 19, 2016.
U.S. Appl. No. 14/054,700, filed Oct. 15, 2013 Advisory Action dated Dec. 15, 2016.
U.S. Appl. No. 14/054,700, filed Oct. 15, 2013 Examiner's Answer dated Jul. 3, 2017.
U.S. Appl. No. 14/054,700, filed Oct. 15, 2013 Final Office Action dated Oct. 19, 2016.
U.S. Appl. No. 14/141,046, filed Dec. 26, 2013 Non-Final Office Action dated Apr. 7, 2017.
U.S. Appl. No. 14/201,300, filed Mar. 7, 2014 Advisory Action dated Mar. 2, 2017.
U.S. Appl. No. 14/201,300, filed Mar. 7, 2014 Final Office Action dated Dec. 19, 2016.
U.S. Appl. No. 14/201,300, filed Mar. 7, 2014 Final Office Action dated Jul. 10, 2017.
U.S. Appl. No. 14/201,300, filed Mar. 7, 2014 Non-Final Office Action dated Mar. 30, 2017.
U.S. Appl. No. 14/548,151, filed Nov. 19, 2014 Final Office Action dated Apr. 19, 2017.
U.S. Appl. No. 14/548,151, filed Nov. 19, 2014 Non-Final Office Action dated Sep. 28, 2016.
U.S. Appl. No. 14/615,932, filed Feb. 6, 2015 Non-Final Office Action dated Dec. 29, 2016.
U.S. Appl. No. 14/846,496, filed Sep. 4, 2015 Non-Final Office Action dated Nov. 25, 2016.
U.S. Appl. No. 15/160,958, filed May 20, 2016 Advisory Action dated Jul. 10, 2017.
CN 201380065663.5 filed Jun. 15, 2015 Office Action dated Oct. 10, 2017.
CN 201480010988.8 filed Aug. 27, 2015 Office Action dated Dec. 13, 2017.
CN 201510144728.6 filed Apr. 17, 2015 Office Action dated Aug. 29, 2017.
CN 201610127217.8 filed Mar. 7, 2016 Office Action dated Dec. 28, 2017.
CN 201610166569.4 filed Dec. 23, 2010, Office Action dated Nov. 1, 2017.
EP 10786978.6 filed Dec. 19, 2011 Office Action dated Aug. 11, 2017.
EP 11827551.0 filed Feb. 7, 2013 Extended European Search Report dated Sep. 19, 2017.

(56) References Cited

OTHER PUBLICATIONS

EP 14197137.4 filed Dec. 10, 2014 Extended European Search Report dated Nov. 4, 2015.
EP 14197137.4 filed Dec. 10, 2014 Office Action dated, Sep. 20, 2017.
EP 14197137.4 filed Dec. 10, 2014, Partial European Search Report dated May 29, 2015.
EP 14761249.3 Filed Sep. 3, 2015 Office Action dated Sep. 28, 2017.
EP 15179061.5 filed Jul. 30, 2015 Partial European Search Report dated Jan. 17, 2018.
JP 2013-530322 filed Mar. 18, 2013, Office Action dated Nov. 6, 2017.
KR 10-2013-7006933 filed Mar. 19, 2013 Office Action dated Aug. 7, 2017.
MX/a/2015/004864 filed Apr. 16, 2015 Office Action dated Dec. 18, 2017.
RU 2015111669 filed Apr. 1, 2015 Office Action dated Sep. 5, 2017.
U.S. Appl. No. 13/887,166, filed May 3, 2013 Appeal Decision dated Aug. 17, 2017.
U.S. Appl. No. 13/887,166, filed May 3, 2013 Notice of Allowance dated Nov. 6, 2017.
U.S. Appl. No. 13/890,158, filed May 8, 2013 Final Office Action dated Nov. 21, 2017.
U.S. Appl. No. 14/141,046, filed Dec. 26, 2013 Final Office Action dated Dec. 11, 2017.
U.S. Appl. No. 14/317,501, filed Jun. 27, 2014 Decision on Appeal dated Nov. 17, 2017.
U.S. Appl. No. 14/548,151, filed Nov. 19, 2014 Advisory Action dated Aug. 1, 2017.
U.S. Appl. No. 14/548,151, filed Nov. 19, 2014 Non-Final Office Action dated Sep. 21, 2017.
U.S. Appl. No. 14/788,305, filed Jun. 30, 2015 Non-Final Office Action dated Jan. 10, 2018.
U.S. Appl. No. 14/788,305, filed Jun. 30, 2015 Restriction Requirement dated Aug. 25, 2017.
U.S. Appl. No. 15/284,355, filed Oct. 3, 2016 Non-Final Office Action dated Nov. 17, 2017.
U.S. Appl. No. 15/365,698, filed Nov. 30, 2016 Non-Final Office Action dated Dec. 14, 2017.
U.S. Appl. No. 15/365,752, filed Nov. 30, 2016 Non-Final Office Action dated Dec. 13, 2017.
Arrow International, Inc., The Arrow-Johans RAECG Adapter-Making Proper Central Venous Catheter Placement More Reliable (Modle No. EG-04900), Technical Report 1987, USA.
B. Braun, Certofix Central Venous Catheter for Placement Using the Seldinger Technique with Simultaneous ECG Lead Option, Feb. 2010.
Colley, Peter S et al, ECG-Guided Placement of Sorenson CVP Catheters via Arm Veins, Anesthesia and Analgesia, pp. 953-956, vol. 63, 1984.
Corsten, et al., "Central Placement Catheter Placement Using the ECG-Guided Cavafix-Certodyn SD Catheter." Journal of Clinical Anesthesiology, vol. 6, Nov./Dec. 1994.
David, et al., "Is ECG-Guidance a Helpful Method to Correctly Position a Central Venous Catheter During Prehospital Emergency Care?" ACTA Anaesthesiologica Scandinavica, vol. 49, pp. 1010-1014, 2005.
Engelhardt, W et al, ECG-Controlled Placement of Central Venous Catheters in Patients with Atrial Anbrallation, Anaesthesist, pp. 476-479, vol. 38 No. 9, Sep. 1989 (Abstract only).
Jeon, Yunseok et al., "Transesophageal Echocardiographic Evaluation of ECG-guided Central Venous Catheter Placement," Canadian Journal of Anesthesia, vol. 53, No. 10, Oct. 1, 2006, pp. 978-983.
Kjelstrup T et al, Positioning of Central Venous Catheters using ECG, Tidssk nor Laegeforen, pp. 599-601, vol. 111 No. 5, Feb. 1999 (Abstract only).

Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.
Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, CHEST, 2003.
McDonnall, "Intra-Atrial Electrocardiography (ECG) for Catheter Placement." Literature review prepared for Bard Access Systems, Oct. 2007.
MedGraphics, CardioPerfect® Resting/Stress ECG System, 3 pages, 2001.
Moureau, Nancy L. et al., "Electrocardiogram (EKG) Guided Peripherally Inserted Central Catheter Placement and Tip Position: Results of a Trial to Replace Radiological Confirmation," Journal of the Association for Vascular Access, pp. 8-14, vol. 15, No. 1, 2010.
Nakatani, K et al, Accurate Placement of Central Venous Catheters—ECG-guided method vs Patient Height Method, Masui, pp. 34-38, vol. 51 No. 1, Jan. 2002.
Pittiruti, et al, "The intracavitary ECG method for positioning the tip of central venous catheters: results of an Italian multicenter study," J Vasc Access, pp. 1-9, Nov. 21, 2011.
Pittiruti, et al, Intracavitary EKG Monitoring: A reliable method for controlling tip position during and after PICC Insertion presentation in Catholic University, Rome, Italy in 2008.
Pittiruti, et al. "The EKG Method for Positioning the Tip of PICCs: Results from Two Preliminary Studies." JAVA, vol. 13, No. 4, pp. 179-185, 2008.
Schafer et al. "Incorrect placement of a vena cava catheter and its prevention by intra-atrial ECG" Anaesthesist. Jan. 1988;37(1):49-51.
Schummer, et al. "Central Venous Catheters—The inability of 'intra-atrial ECG' to prove adequate positioning." British Journal of Anaesthesia, vol. 93, No. 2, pp. 193-198, 2004.
Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).
Schummer, W et al, Intra-Atrial ECG is not a Reliable Method for Positioning Left Internal Jugular Vein Catheters, Br J Anaesth, pp. 481-486, vol. 91 No. 4, Oct. 2003.
Schummer, W, Central Venous Catheter—The Inability of "Intra-Atrial ECG" to prove Adequate Positioning, Br J Anaesth, pp. 193-198, vol. 93 No. 2, Aug. 2004.
Starr, David S et al, EKG Guided Placement of Subclavian CVP Catheters Using J-Wire, pp. 673-676, Ann. Surg, Dec. 1986.
Tepa® Health Innovation PC based ECG System Introduction and Technical Specifications, EKG Master USB, 2 pages, Nov. 2003.
Welch Allyn Cardioperfect® PC-Based Resting ECG, 2003.
Zachariou, Zacharias et al., Intra-atrial ECG recording: a new and safe method for implantation of Broviac catheters in children, Pediatr Surg Int (1994) 9: 457-458.
U.S. Appl. No. 15/160,958, filed May 20, 2016 Final Office Action dated Apr. 21, 2017.
U.S. Appl. No. 15/160,958, filed May 20, 2016 Non-Final Office Action dated Dec. 15, 2016.
U.S. Appl. No. 15/160,958, filed May 20, 2016 Notice of Allowance dated Jul. 26, 2017.
U.S. Appl. No. 15/284,355, filed Oct. 3, 2016 Non-Final Office Action dated Apr. 24, 2017.
U.S. Appl. No. 15/585,051, filed May 2, 2017 Non-Final Office Action dated Jul. 14, 2017.
AZoMaterials. Nickel-Based Super Alloy Inconel 625—Properties and Applications by United Performance Alloys. Oct. 27, 2015. Last accessed Mar. 23, 2018. <URL:https:I/web.archive.org/web/20151027202821/https://www.azom.com/article.aspx?ArticleID=4461>.
CA 2800810 filed Nov. 26, 2012 Office Action dated Mar. 13, 2018.
CA 2800813 filed Nov. 26, 2012 Office Action dated Mar. 5, 2018.
CN 2013800511725 filed Mar. 30, 2015 Office Action dated Jan. 16, 2018.

(56) References Cited

OTHER PUBLICATIONS

CN 2013800511725 filed Mar. 30, 2015 Office Action dated Jul. 30, 2018.
CN 201480010988.8 filed Aug. 27, 2015 Office Action dated Aug. 17, 2018.
CN 201610127217.8 filed Mar. 7, 2016 Office Action dated Jun. 11, 2018.
Enrique Company-Bosch, "ECG Front-End Design is Simplified with MicroConverter." Analog Dialogue 37-11, (dated Nov. 2003).
EP 11850625.2 filed Jul. 22, 2013 Office Action dated Sep. 24, 2018.
EP 14197137.4 filed Dec. 10, 2014 Office Action dated Apr. 5, 2018.
EP 17186624.7 filed Aug. 17, 2017 Extended European Search Report dated Jan. 17, 2018.
EP 17186624.7 filed Aug. 17, 2017 Partial European Search Report dated Jan. 17, 2018.
Hamza, N. et al. "Interference reduction in ECG signal acquisition: Ground electrode removal." 2013 International Conference on Computer Medical Applications (ICCMA), Jan. 2013.
Honeywell, "1, 2 and 3 Axis Magnetic Sensors HMC1051/HMC1052L/HMC1053" dated Jan. 2010.
JP 2013-530322 filed Mar. 18, 2013, Office Action dated Jul. 6, 2018.
JP 2015-534770 filed Mar. 26, 2015 Office Action dated Feb. 21, 2018.
KR 10-2014-7002789 filed Feb. 3, 2014 Office Action dated Jun. 21, 2018.
MX/a/2015/004864 filed Apr. 16, 2015 Office Action dated Apr. 24, 2018.
Not Resource Center. Magnetic Permeability. Oct. 18, 2014. Last accessed Mar. 23, 2018. <URL:https://web.archive.org/web/20141018213902/https://www.nde-ed.org/EducationResources/CommunityCollege/Materials/Physical_Chemical/Permeability.htm>.
PCT/US2017/066503 filed Dec. 14, 2017 International Search Report and Written Opinion dated Feb. 20, 2018.
RU 2015111669 filed Apr. 1, 2015 Office Action dated Jan. 25, 2018.
RU 2015111669 filed Apr. 1, 2015 Office Action dated May 18, 2018.
Thakor, N. V., et al. "Ground-Free ECG Recording with Two Electrodes." IEEE Transactions on Biomedical Engineering, vol. BME-27, No. 12, Dec. 1980.
U.S. Appl. No. 13/665,420, filed Oct. 31, 2012 Notice of Allowance dated Feb. 7, 2018.
U.S. Appl. No. 13/890,158, filed May 8, 2013 Advisory Action dated Feb. 13, 2018.
U.S. Appl. No. 13/890,158, filed May 8, 2013 Notice of Allowance dated May 30, 2018.
U.S. Appl. No. 14/141,046, filed Dec. 26, 2013 Examiner's Answer dated Oct. 15, 2018.
U.S. Appl. No. 14/201,300, filed Mar. 7, 2014 Examiner's Answer dated Apr. 19, 2018.
U.S. Appl. No. 14/317,501, filed Jun. 27, 2014 Notice of Allowance dated Feb. 9, 2018.
U.S. Appl. No. 14/788,305, filed Jun. 30, 2015 Final Office Action dated Jul. 27, 2018.
U.S. Appl. No. 15/192,561, filed Jun. 24, 2016 Non-Final Office Action dated Apr. 6, 2018.
U.S. Appl. No. 15/284,355, filed Oct. 3, 2016 Advisory Action dated Aug. 13, 2018.
U.S. Appl. No. 15/284,355, filed Oct. 3, 2016 Final Office Action dated May 24, 2018.
U.S. Appl. No. 15/365,698, filed Nov. 30, 2016 Final Office Action dated Jul. 12, 2018.
U.S. Appl. No. 15/365,734, filed Nov. 30, 2016 Non-Final Office Action dated Feb. 23, 2018.
U.S. Appl. No. 15/365,734, filed Nov. 30, 2016 Notice of Allowance dated Jun. 4, 2018.
U.S. Appl. No. 15/365,752, filed Nov. 30, 2016 Final Office Action dated Jul. 12, 2018.
U.S. Appl. No. 15/365,872, filed Nov. 30, 2016 Non-Final Office Action dated Aug. 27, 2018.
U.S. Appl. No. 15/365,872, filed Nov. 30, 2016 Restriction Requirement dated Apr. 5, 2018.
U.S. Appl. No. 15/585,051, filed May 2, 2017 Final Office Action dated Feb. 28, 2018.
U.S. Appl. No. 15/585,051, filed May 2, 2017 Final Office Action dated Mar. 15, 2018.
U.S. Appl. No. 15/900,623, filed Feb. 20, 2018 Final Office Action dated Sep. 20, 2018.
U.S. Appl. No. 15/900,623, filed Feb. 20, 2018 Non-Final Office Action dated May 3, 2018.
CN 201580007645.0 filed Aug. 8, 2016 Office Action dated Sep. 12, 2018.
CN 201610127217.8 filed Mar. 7, 2016 Office Action dated Nov. 19, 2018.
EP 10786978.6 filed Dec. 19, 2011 Office Action dated Jan. 16, 2019.
EP 14197137.4 filed Dec. 10, 2014, Office Action dated Nov. 21, 2018.
EP 15746326.6 filed Jul. 1, 2016 Office Action dated Jan. 29, 2019.
EP14197136.6 filed Dec. 10, 2014 Office Action dated Nov. 21, 2018.
RU 2015110633 filed Mar. 26, 2015 Office Action dated Oct. 25, 2018.
U.S. Appl. No. 14/788,305, filed Jun. 30, 2015 Advisory Action dated Oct. 19, 2018.
U.S. Appl. No. 14/788,305, filed Jun. 30, 2015 Notice of Allowance dated Nov. 15, 2018.
U.S. Appl. No. 15/192,561, filed Jun. 24, 2016 Final Office Action dated Nov. 1, 2018.
U.S. Appl. No. 15/365,752, filed Nov. 30, 2016 Notice of Allowance dated Nov. 6, 2018.
U.S. Appl. No. 15/365,872, filed Nov. 30, 2016 Notice of Allowance dated Dec. 21, 2018.
EP 11850625.2 filed Jul. 22, 2013 Office Action dated Feb. 25, 2019.
KR 10-2014-7002789 filed Feb. 3, 2014 Office Action dated Feb. 22, 2019.
U.S. Appl. No. 14/040,205 filed Sep. 27, 2013 Board Decision dated May 1, 2019.
U.S. Appl. No. 14/054,700 filed Oct. 15, 2013 Board Decision dated May 1, 2019.
U.S. Appl. No. 14/201,300 filed Mar. 7, 2014 Board Decision dated Apr. 12, 2019.
U.S. Appl. No. 14/996,247 filed Jan. 15, 2016 Restriction Requirement dated Mar. 22, 2019.
U.S. Appl. No. 15/284,355 filed Oct. 3, 2016 Notice of Allowance dated Feb. 21, 2019.
U.S. Appl. No. 15/365,698 filed Nov. 30, 2016 Non-Final Office Action dated Apr. 18, 2019.
U.S. Appl. No. 15/585,051 filed May 2, 2017 Examiner's Answer dated May 2, 2019.

DEVICES AND METHODS FOR ENDOVASCULAR ELECTROGRAPHY

CROSS-REFERENCE TO RELATED APPLICATIONS

This application is a division of U.S. patent application Ser. No. 12/854,083, filed on Aug. 10, 2010, now U.S. Pat. No. 9,445,734, which is a continuation-in-part (CIP) of U.S. patent application Ser. No. 12/815,331, filed on Jun. 14, 2010, now U.S. Pat. No. 9,339,206, which claims priority to U.S. Provisional Patent Application No. 61/213,474, filed on Jun. 12, 2009, the disclosures of which are incorporated herein by reference in their entirety. This application also claims the benefit of U.S. Provisional Patent Application No. 61/272,025, filed on Aug. 10, 2009, the disclosure of which is incorporated herein by reference in its entirety.

FIELD OF THE INVENTION

The present invention relates to endovascular device positioning. Specifically, the present invention relates to an adapter for an endovascular device and a steering device for a catheter.

BACKGROUND

The electrical conduction system of the heart creates specific electrical signals, electrical energy distributions and behaviors thereof which are indicative of specific locations in the thoracic cavity and/or of specific heart functions or conditions. When measured endovascularly, i.e., from within blood vessels or from within the heart, certain parameters of the electrical activity of the heart can be used to identify specific locations in the cardiovascular system and/or functional conditions, normal or abnormal. Moreover, by locally and accurately identifying the location and the type of condition, therapy of such conditions can be optimized and the effect of the therapy monitored in real-time.

Two types of clinical applications are typically addressed. The first is related to guiding endovascular devices through the cardiovascular system, while the second is related to the non-invasive or the minimally invasive remote monitoring of the electrical activity of the heart.

The guidance, positioning, and placement confirmation of endovascular catheters are necessary in a number of clinical applications, such as, for example:
 1. Central venous access, e.g., CVC, PICC, implantable ports;
 2. Hemodialysis catheters;
 3. Placement of pacemaker leads;
 4. Hemodynamics monitoring catheters, e.g., Swan-Ganz and central pressure monitoring catheters; and
 5. Guiding guidewires and catheters into the left heart.

The location of the catheter tip is very important to the patient safety, the duration and the success of the procedure. Today's golden standard for confirming the target location of the catheter tip is the chest X-ray. In addition, there are currently two types of real-time guiding products available on the market, which try to overcome the limitations of chest X-ray confirmation: electromagnetic and ECG-based. In hospitals where real-time guidance is used results have improved in terms of reducing the number of X-rays, the procedure time, and the cost of the procedure. Under real-time guidance first-time success rate has typically increased from 75%-80% to 90%-95%. In addition, in hospitals where ECG guidance is used, e.g., in Italy, Belgium, Germany, chest X-ray confirmation has been eliminated for more than 90% of the patients. Electromagnetic systems are used mostly in the United States while ECG-based systems are used mostly in Europe. Amongst other factors which determine the difference between the markets in the United States and Europe in terms of technology adoption: a) type of health care personnel allowed to perform procedures: nurses have more flexibility in the United States, b) type of devices placed: PICCs are placed more and more often in the United States, c) price sensitivity: the European market seems to be more price sensitive, and d) the current guiding devices are commercialized by specific manufacturers to work exclusively with their catheters: market penetration of the guiding systems reflects the market penetration of the catheter manufacturer.

It was also found that different opinions exist regarding where the target tip location should be: for example, lower third of the SVC or RA. Therefore guiding technologies should allow for discrimination of these locations. The chest X-ray, which is the current golden standard does not always allow for such discrimination requiring an accuracy of typically better than 2 cm. Also, because ECG-based systems make use of physiological information related to the heart activity, their ability to guide placement is accurate with respect to the anatomy. This is not the case with electromagnetic guiding systems which measure the distance between the catheter tip in the vasculature and an external reference placed typically on the patient's chest. Because of this aspect, ECG-based systems can be used to document the final result of the catheter placement potentially replacing the chest X-ray as the golden standard.

One of the most valuable diagnostic tools available, the ECG records the heart's electrical activity as waveforms. By interpreting these waveforms, one can identify rhythm disturbances, conduction abnormalities, and electrolyte imbalance. An ECG aids in diagnosing and monitoring such conditions as acute coronary syndromes and pericarditis. The heart's electrical activity produces currents that radiate through the surrounding tissue to the skin. When electrodes are attached to the skin, they sense these electrical currents and transmit them the electrocardiograph. Because the electrical currents from the heart radiate to the skin in many directions, electrodes are placed at different locations on the skin to obtain a total picture of the heart's electrical activity. The electrodes are then connected to an electrocardiograph device, or computer, and record information from different perspectives, which are called leads and planes. A lead provides a view of the heart's electrical activity between two points or poles. A plane is a cross section of the heart which provides a different view of the heart's electrical activity. Currently, the interpretation of an ECG waveform is based on identifying waveform component amplitudes, analyzing and then comparing the amplitudes with certain standards. Modifications of these amplitude components are indicative of certain conditions, e.g., the elevation of the ST segment or of certain locations in the heart, e.g., the amplitude of the P-wave. In today's practice ECG monitors are widely used to record ECG waveforms. More and more often applications are made available for automatic identification of the ECG amplitude components. In certain cases tools are available for decision making support and for automatic interpretation of ECG amplitude components with respect to underlying heart conditions.

Remote patient monitoring is a well-established medical field. Still remote monitoring of heart conditions is not as widely accepted as it would be need and possible. One of the reasons is related to the relatively complicated way of acquiring signals related to the heart activity, in particular ECG signals. Another important limiting factor of the current remote monitoring technologies is the use of communications channels, like the telephone line, which are difficult to interface with at both the patient and the physician ends.

SUMMARY OF THE INVENTION

Embodiments of the present invention advantageously provide an adapter for an endovascular device and a steering device for a catheter.

According to one embodiment of the present invention, an adapter for an endovascular device includes a body, a conductive metal ring and a conductive wire. The body includes a first open end, a second open end, a central lumen having a substantially cylindrical surface extending from the first open end to the second open end, and a channel extending from the central lumen to an external opening. The conductive metal ring is attached to the surface of the central lumen, and the conductive wire is coupled to the conductive metal ring and extends through the channel and the external opening.

According to another embodiment of the present invention, a steering device for a catheter that has a plurality of lumens with spaced distal openings includes a stylet for disposition within one of the plurality of lumens, and a steering member for disposition within a different one of the plurality of lumens. In the installed position, the stylet and the steering member are connected together at respective distal ends such that a portion of the steering member is disposed outside of the distal end of the catheter.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF DRAWINGS

FIG. 4A depicts a single lead configuration, FIG. 4B depicts a modified 3-lead configuration with monitoring and guiding capabilities, FIG. 4C depicts a telemetry configuration with a single grounded lead, and FIG. 4D depicts one use of ECG monitors for guiding endovascular devices.

DETAILED DESCRIPTION

Figure 1A:
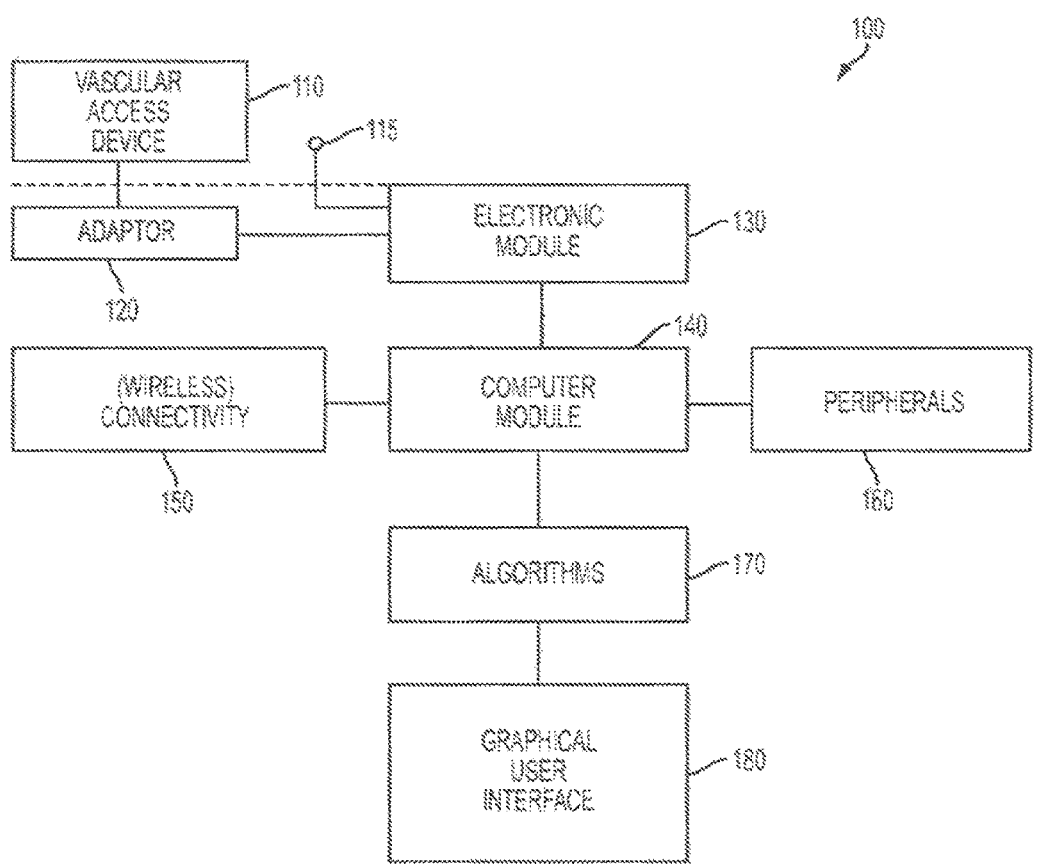
FIG. 1A is a block diagram that depicts an apparatus according to an embodiment of the present invention.

The invention will now be described with reference to the drawing figures, in which like reference numerals refer to like parts throughout.

Embodiments of the present invention advantageously provide an inventive apparatus(es), computer-based data processing algorithms and methods for obtaining and using endovascular ECGs in a number of clinical applications and settings. For example, once device can be used to guide endovascular devices in and around the heart, e.g., guiding central venous access devices in the superior vena cava, right atrium, and right ventricle. Such central venous access devices may include central venous catheters (CVC), peripherally inserted central catheters (PICC), implantable ports, hemodialysis catheters, tunneled catheters and others. Other devices which may benefit from guidance with the inventive apparatus are temporary pacemaker leads placed through the central venous system. Catheters and guidewires used in left heart procedures may also benefit from the present invention by decreasing the amount of contrast and radiation required to guide these devices in position. In another example, the apparatus can be used for minimally invasive monitoring and assessing heart conditions based on its electrical activity, e.g., assessing preload in a heart cycle or monitoring ST segments and T-waves in congestive heart failure.

In one aspect of the invention, an apparatus is described consisting of sterile adaptors, an electronic module for signal acquisition, a computer module, software, and peripheral devices and connections. In one embodiment, the electronic module for signal acquisition can be dedicated to acquiring and processing endovascular electrical signals generated by the body (endovascular ECG), in another embodiment the electronic module can be dedicated to acquiring and processing endovascular ECGs as well as skin ECGs.

In one embodiment, the electronic module and the computer module can be separate modules, in another embodiment they can be integrated in the same module and enclosure, and yet in another embodiment they can communicate with each other via a wireless connection, such as Bluetooth. In one embodiment, the apparatus can contain an integrated printer, while in another embodiment the printer can be external and attached to the apparatus and the apparatus connected via network, e.g., wireless to other devices. In yet another embodiment the apparatus can be used for telemetry and for transmitting the endovascular electrograms to a remote location, e.g., via a telephone line, Internet, and/or wireless phone. Any combination of embodiments mentioned above is also possible.

In another aspect of the invention, various configurations allow the connection of endovascular devices, such as central venous access devices, to the electronic module for signal acquisition and processing. In one embodiment, the device consists of a connecting wire with two ends and special connectors at each end. At one end, the wire can be connected to a metal or nitinol guidewire or stylet as commonly available on the market. At the other end, the wire can be safely connected to the electronic module. In another embodiment, the device includes a coated guidewire, e.g., made of nitinol or stainless steel with uncoated distal and proximal ends and cm markings. In such an embodiment, the coated guidewire is inserted endovascularly, while the connecting wire is connected to the proximal end of the coated guidewire. In another embodiment, the device includes a catheter-syringe adaptor provided with an electrical connecting wire. At one end, the electrical connecting wire is in contact with the fluid, e.g., saline flowing within the catheter syringe adapter. At the other end the connecting wire can be connected to the electronic module.

In another aspect of the invention, various electrode configurations allow for the optimal acquisition of endovascular ECGs. In one embodiment, a single lead is used to provide information about the tip location of an endovascular device within the vasculature. In another embodiment a modified three lead configuration is used to provide simultaneous 3-lead monitoring of the heart activity at the same time with providing tip location information. In another embodiment a modified single lead configuration plus ground is used for telemetry and transferring information from the tip of the catheter remotely.

In another aspect of the invention algorithms are introduced for the analysis of the ECG waveforms and for supporting decision making based on these waveforms. These algorithms discriminate between different locations in the vasculature and assess body functions (systemic and at specific locations in the body), in particular heart functionality. In various embodiments, these algorithms use time domain analysis of waveforms: morphologic, for example shape; statistic, for example behavior.

In other embodiments, the algorithms use frequency domain analysis of waveforms: morphologic, for example shape; statistic, for example behavior. In further embodiments, signal energy analysis in time and frequency domains is also performed, morphologic and statistic. Fuzzy, statistical, and knowledge-based decision making are also contemplated by the present invention as decision support tools.

In another aspect of the invention, a user interface is provided that advantageously simplifies interpretation of data and workflow. In one embodiment the user interface includes simplified graphics showing the location in the vasculature and in the heart of the tip of the endovascular device in use without showing any of the ECG waveforms. In another embodiment, the user interface shows, in real-time, the change in location of the tip of the endovascular device in use.

In another aspect of the invention, several inventive methods are presented which use the apparatus described herein in clinical applications. In one embodiment, a computer-based method is provided that guides central venous catheters (CVC, PICCs, hemodialysis, implantable ports, and others) using stylets, guidewires and saline solution to the superior vena cava, inferior vena cava, the right atrium, and the right ventricle. This method is advantageously less sensitive to patients with arrhythmias than the prior art, and represents an alternative to chest X-ray confirmation of tip location of central venous catheters in most clinical cases. In another embodiment, a computer-based method is provided that guides coated guidewires in the right and left heart. In another embodiment, a computer-based method is provided that guides the placement of temporary pacemaker leads through the central venous system. In another embodiment, a method is provided that is minimally invasive and monitors preload using depolarization and heart rhythms. In another embodiment, a method is provided that is minimally invasive and monitors arrhythmias using P-wave analysis. In another embodiment, a method is provided that is minimally invasive and monitors heart failure using ST segment and T-wave analysis.

FIG. 1A is a block diagram that depicts an apparatus according to an embodiment of the present invention.

The apparatus 100 can be attached through an adaptor (120) to a large variety of commercially available and custom designed vascular access devices (110). Examples of such devices are: central venous catheters (CVC), peripherally inserted central catheters (PICC), implantable ports, tunneled catheters, hemodialysis catheters, guiding catheters for pacemaker leads, guidewires used for coronary and other vascular interventions, guiding catheters for coronary and other vascular interventions, stylets, syringe needles, and others. If the vascular access devices is a stylet, a guidewire, or a syringe needle, its material must be sufficiently electrically conductive, e.g., stainless steel or nitinol. In such a case the hook or the alligator clip adaptor according to the present invention should be used. If the vascular access devices is a catheter, than saline should be used to establish a conductive path through one of the catheter's lumens. In such a case, the syringe-catheter adaptor according to the present invention should be used.

The electronic module (130) receives electrical signals from the adaptor and from one or more other electrodes placed on the patient's skin (115). Alternatively, more than one adaptor can be used at the same time to connect to more than one endovascular device in order to provide different electrical signals to the electronic module. The use of skin electrodes is optional in certain device configurations. The electronic module processes the electrical signals and transmits them to a computer module (140) for further processing and other functions. In one embodiment the electronic module and the computer module can be packaged separately, in another embodiment they can be integrated in the same package. In one embodiment the connection between the electronic module and the computer module can be hardwired, in another embodiment it can be wireless, e.g., using Bluetooth.

The computer module processes the signals from the electronic module applying algorithms (170) as described by the current invention. The computer module can also be connected to peripherals (160), e.g., a printer or a label printer and storage devices and provides connectivity including wireless connectivity (150) to other computers or to the internet. The storage device can be used to store a database of know ledge and information regarding the application at hand. The connectivity interface can be used to update this database remotely with newest relevant knowledge and information, e.g., new clinical cases, new findings regarding the relationship between electrograms and heart conditions. The computer module supports a graphical user interface (180) optimized for the purpose of the clinical application at hand.

Figure 1B:
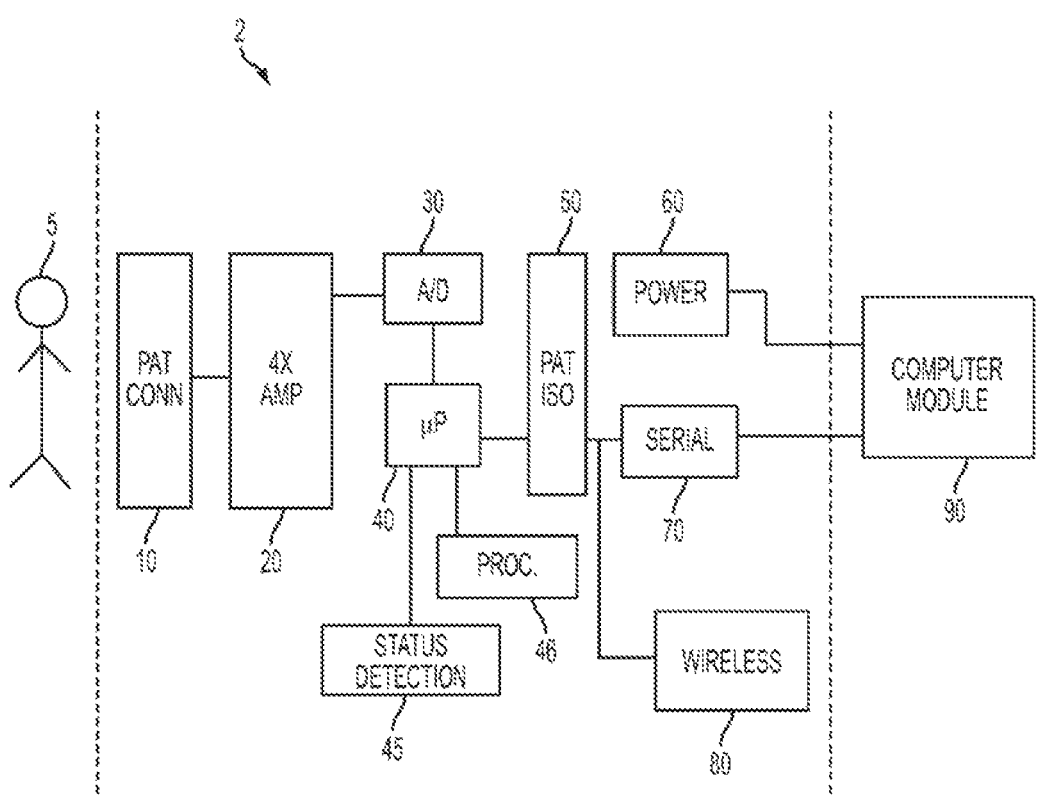
FIG. 1B is a block diagram of an electronic module for acquisition and processing of endovascular electrocardiogram according to an embodiment of the present invention.

FIG. 1B is a block diagram of an electronic module (2) for acquisition and processing of endovascular electrocardiogram according to an embodiment of the present invention.

The patient connector interface (10) allows for connecting electrical leads to the patient (5). Any combination of skin electrodes and/or electrical connections to endovascular devices using the adaptors discussed above can be used. In one embodiment, the amplifier (20) is a four stage amplifier with variable gain, which can amplify electrical signals coming through the patient cable, for example, typical of electrocardiographic values. The analog-to-digital converter (30) converts the signals in digital format readable by the microprocessor (40). Any number and configurations of microprocessors, microcontrollers, or digital signal processors can be used to implement the micro-processing function (45).

In one embodiment, a microcontroller is responsible for controlling the serial communication with a computer module (90) via the serial interface (70) or via the wireless interface (80) and a digital signal processor (DSP) is responsible for implementing one or several of the inventive algorithms described herein. Alternatively, a single processor (46) can be used for both communication and processing.

The micro-processor (40) also receives commands from the computer module (90) and controls different elements of the electronic module, e.g., the amplifier (20) accordingly. The patient isolation block (50) decouples electrically the power (60) and the serial communication channel (70) from the patient interface (10) in order to ensure patient protection to electrical shock. In one embodiment the isolation block (50) can consists of a transformer and/or couplers, e.g. optical couplers.

Figure 2:
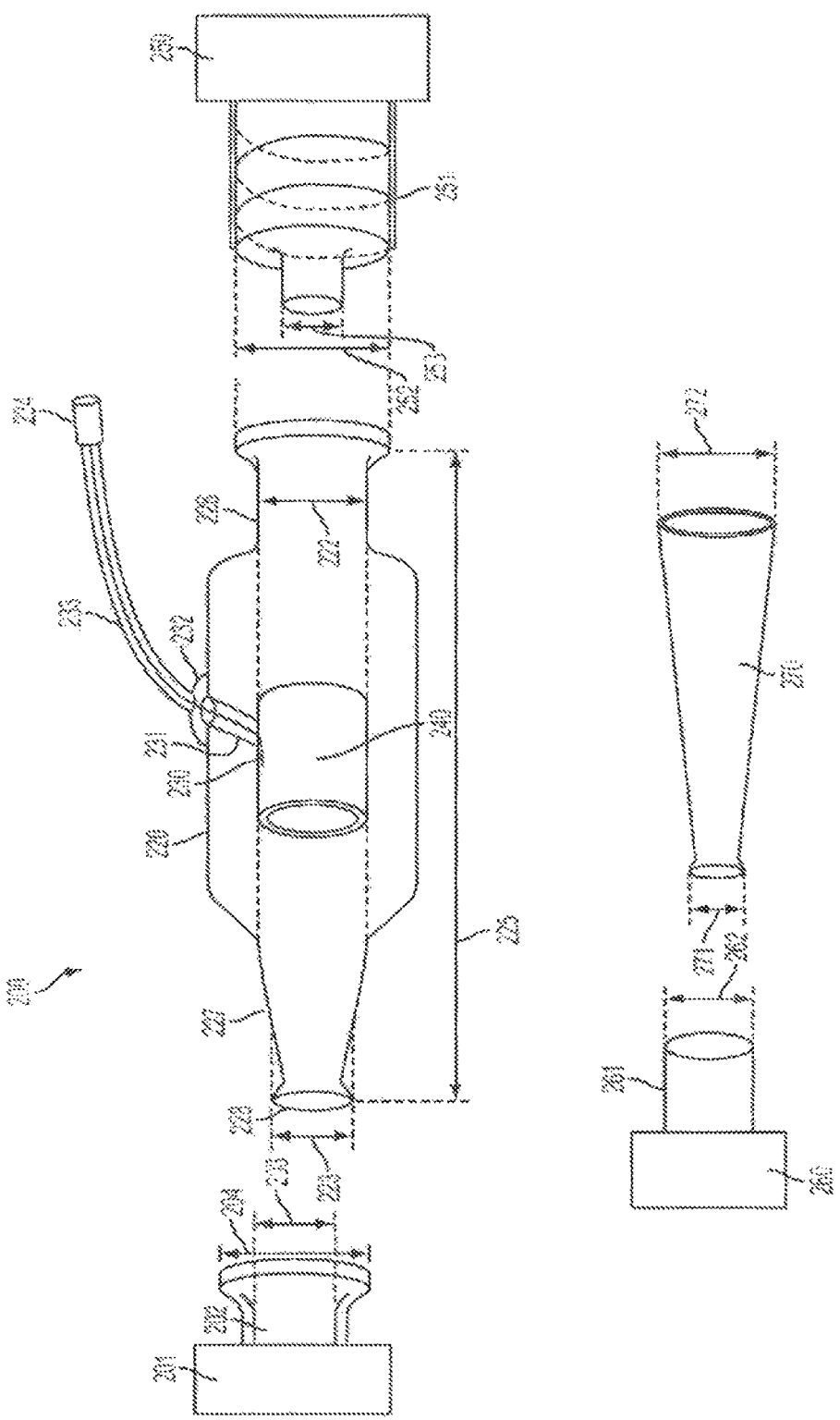
FIG. 2 depicts an adaptor for an endovascular device according to an embodiment of the present invention.

FIG. 2 depicts an adaptor (200) for an endovascular device according to an embodiment of the present invention. Vascular access devices like catheters, syringes, syringe needles, stopcocks, infusion pumps and others connect to each other through standard connections. For example, in FIG. 2 such a standard connection between two devices is illustrated on device (201) by the luer (202) with inner diameter (203) and outer diameter (204), and on device (250) by threaded port (251) with inner diameter (252) and fluid opening diameter (253). The threaded port (251) and the luer (202) allow for connecting the two devices (201, 250) by threading, attaching, coupling, etc., the port (251) into the luer (202).

The adaptor (200) has a body (220) with two ends (226, 227) with a length 225, and is made, for example, of strong biocompatible plastic material with some degree of elasticity. End (227) has a shape of a cone. In one embodiment, end (227) has an elastic sealing portion (228) such that end (227) can easily fit in the luer (202) of device (201) to seal the connection for fluid flow. The other end (226) is in the shape of a standard luer, such as, for example, luer (202) of device (201). The threaded port (251) of the device (250) can be connected to end (226) of the adaptor (200). The cone piece (227) also allows a connection to a device that does not have a luer. The stand-alone cone piece (270) allows a connection between two devices with different accessible diameters. The end (227) of adaptor (200) has a diameter (223) and fits inside the diameter (272) of the cone piece (270). The end (271) of the cone piece (270) fits in a simple catheter end portion (261) with a diameter (262) of a typical device (260). For example, device (260) can be a catheter for an implantable port.

In one embodiment, device (201) is a syringe needle, and device (250) is a syringe. Fluid, e.g., a conductive electrolyte, flows through adaptor (200) through a central inner bore or lumen (222) having a certain diameter, and provides a fluid path between the devices (250, 201). A conductive metal ring (240) is attached to a portion of the substantially cylindrical surface of lumen (222) and, preferably, induces very little perturbations to the fluid flow. For example, the metal ring (240) may be disposed within a recessed portion of the substantially cylindrical surface of the lumen (222). One end (230) of a conductive wire (233) is electrically coupled to the metal ring (240); in one embodiment, the end (230) is soldered to metal ring (240). In another embodiment, the end (230) is captured between the surface of the lumen (222) and the metal ring (240), and the end (230) and the metal ring (240) maintain good electrical contact through mechanical pressure. The wire (233) may be bare or insulated. In a preferred embodiment, the metal ring (240) is fixedly attached to the surface of lumen (222) using, for example, adhesive, an interference fit, a press fit, etc., while in other embodiments, the metal ring (240) may be removably attached to the surface of lumen (222), free-floating, etc.

The wire (233) passes through a channel (231), which extends from the lumen (222) to an opening in the outer surface of the body (220). Epoxy (232), or other suitable material, may be used to seal the opening of the channel (231), as well as to provide a strain relief for the wire (233). The metal ring (240) may be advantageously disposed adjacent to the channel (231) to provide additional sealing. Thus, the metal ring (240), the wire (233), the channel (231) and the epoxy (232) provide a sealed, electrical connection to the fluid flowing through the adaptor (200). A connector (234) may provide a standard electrical connection to the electrography system; a non-terminated wire may also be used. In one embodiment, the wire (233) terminates at the opening of the channel (231) and the connector (234) is attached directly to the body (222), while in another embodiment, the wire (233) extends through the opening of the channel (231) and the connecter (234) is attached to the free end of the wire (233).

In one embodiment, the substantially cylindrical surface of lumen (222) is tapered along the longitudinal direction.

This taper may extend along the entire length of lumen (222), or restricted to a certain portion thereof. For example, the surface of lumen (222) may be cone-shaped and have a larger diameter at the proximal end, or, alternatively, the larger diameter may be located at the distal end.

In one example, device (201) is a syringe needle that is inserted into a lumen of a catheter for an implantable port, and device (250) is a syringe. The syringe is filled with saline, which is then injected into the catheter through the adaptor (200). Thus, the adaptor (200) becomes filled with saline solution, and, because the conductive metal ring (240) is in contact with saline and the conductive wire (233), an electrical connection is established between the catheter lumen and the wire (233). In this way, the electrical signal at the tip of the catheter may be measured through the saline solution. Other electrically conductive solutions may also be used to obtain the endovascular electrogram using the adaptor (200). In another embodiment, the adaptor (200) may be used with infusion pumps, as well as other types of power injections. In an alternative embodiment, the adaptor (200) does not include the metal ring (240), and the electrically conductive ending (230) is in direct contact with the electrolyte.

Figure 3:
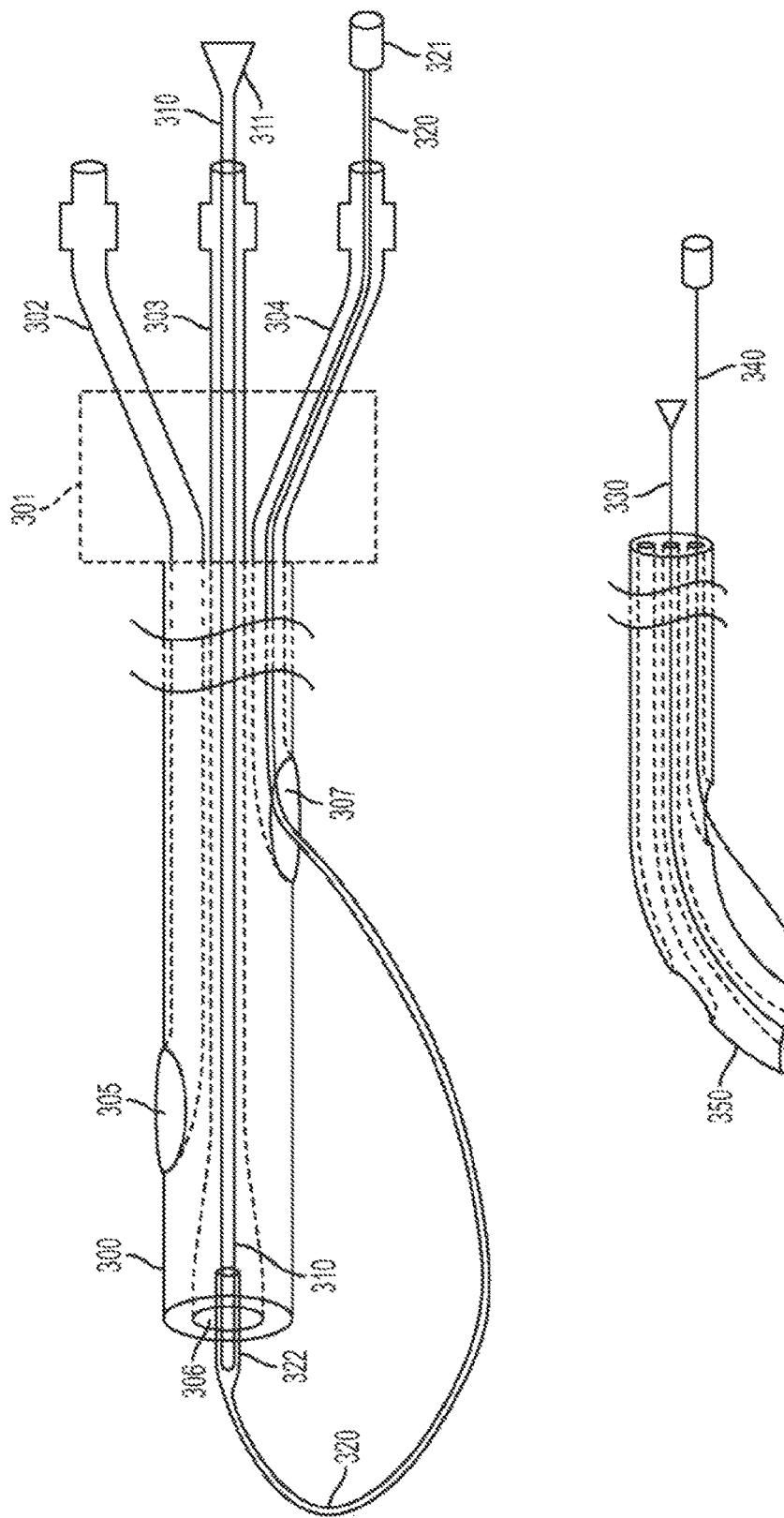
FIG. 3 depicts a catheter steering device according to an embodiment of the present invention.

FIG. 3 illustrates a catheter steering device according to an embodiment of the present invention. In this embodiment, the catheter (300) is a triple lumen catheter and the distal end of each of the lumens is spaced with respect to each other. The catheter steering device can be used with any catheter having two or more lumens with spaced distal lumen openings. The open end of one lumen (306) of catheter (300) is at the very distal end of the catheter, another end or opening of a lumen (305) is spaced back from the distal end and the end or opening of the third lumen (307) is spaced back compared to the second end (305). The distance between the open end (306) and the end (307) is typically from one to several centimeters.

Several types of catheters have multiple lumens with spaced ends, and the inventive steering device can accommodate such catheters. For example, in the case of a peripherally inserted central catheter, the typical length of a catheter is 50 to 60 centimeters and the spacing between the distal lumen ends (305, 306, and 307) is from one to several centimeters. A hemodialysis catheter with two lumens can typically be 20 to 40 centimeters in length, with one to several centimeters spacing between the distal ends of the two lumens. A multi-lumen central venous catheter (CVC) can typically be 15 to 25 cm in length with spacing between distal ends or openings of the lumens being from several millimeters to several centimeters.

At the proximal end, the catheter has a catheter hub (301) which splits the three lumens and connects each of them with a luer (302, 303, 304). The inventive catheter steering device includes a stylet (310) with a handle (311) at the proximal end to allow for pushing, pulling, and removal after use, and a steering member (320) which connects to the distal end of the stylet (322) and which can be fed back into a distal lumen opening of one of the other lumens, such as, for example, lumen (307). The steering member (320) returns to the proximal end of the catheter through the catheter lumen and exits at the proximal end through the luer corresponding the respective lumen (304). So disposed, the steering device is in the installed position. In one embodiment, the member (320) has a handle (321) which can be used to pull the member through the lumen. In another embodiment, the handle (321) is detachable from the member (320).

The member (320) may be polyurethane, silicone, PTFE, or other similar materials. In different embodiments, the member (320) may be any kind of biocompatible thread, e.g., surgical thread. In another embodiment, the member (320) is stainless steel wire. In one embodiment, the stylet is provided pre-inserted into one of the catheter lumens, typically the central lumen with the most distal opening (306) with the member 320 attached at the distal end of the stylet (322) and pre-inserted into the lumen (304) through the lumen opening (307). In order to steer the catheter, the user pulls the member 320 out of the catheter while preventing the stylet 310 to be pulled into the catheter. Thus, the catheter tip can be bent in a desired direction. This situation is illustrated by the bent catheter tip (350), the member (340) which was pulled back and the member (330) which is its initial position with respect to the catheter. If the stylet (310) or the steering member (320), or both are made of any electrically conductive material, then each or both of them can be used to measure electrical signals or endovascular electrograms at the distal tip of the catheter by connecting their proximal ends to the endovascular electrography system. In one embodiment, the steering member (320) can be tied to the stylet (310) through the opening (307) of the catheter lumen.

In another embodiment, the stylet (310) and the steering member (320) are manufactured as a single component to form an extended steering member that is looped back through the opening (305) of a different catheter lumen. By pulling one of the two ends of the extended steering member coming out through luers (304) and (302), the same effect is achieved and the catheter tip can be bent in a desired direction. In another embodiment, in the case of a double lumen catheter, the stylet (310) can be inserted in one lumen and the steering member (320) can be inserted in the other lumen, such that the effect of bending the catheter tip can be achieved by pulling the proximal ends. In a further embodiment, the steering member (320) can be inserted in the lumen (302) and through the opening (305).

FIGS. 4A, 4B, 4C, and 4D depict electrode configurations that provide optimal acquisition of endovascular electrocardiogram according to various embodiments of the present invention.

Figure 4A:
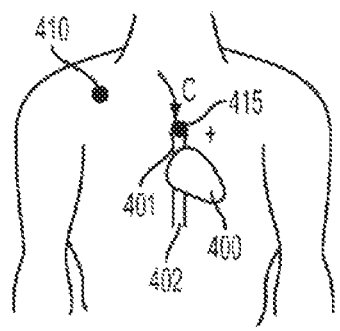
FIGS. 4A, 4B, 4C, and 4D depict electrode configurations that provide optimal acquisition of endovascular electrocardiogram according to various embodiments of the present invention.

FIG. 4A depicts a single lead configuration with a reference electrode (410), for example attached to the patient's skin over the right arm and with the other electrode attached through an adaptor to an endovascular device (415). The reference electrode attached to the skin over the right arm is presented in this configuration for illustration purposes only. Other locations of the reference electrode are possible depending on the type of ECG required. The reference electrode over the right arm together with the tip of the endovascular device used with the adaptor can be similar to lead II of a standard ECG. In this case the ECGs obtained from the superior vena cava (401) and inferior vena cava (402) can be optimized. The reference electrode can be attached to the skin in any other location in order to simulate other leads of the standard ECG. The reference electrode can be also connected to adaptors attached to other endovascular devices in order to obtain more local information from within the patient's heart (400).

Figure 4B:
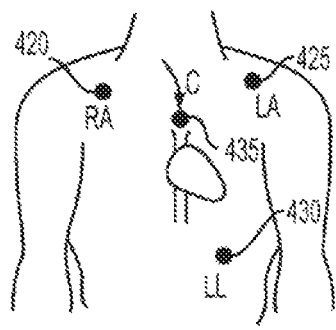

FIG. 4B depicts a modified 3-lead configuration, with monitoring and guiding capabilities, with 4 electrodes. Three (3) electrodes correspond to the standard ECG electrodes: right arm (RA, 420), left arm (LA, 425), and left leg (LL, 430) used as reference. The fourth electrode is attached through an adapter to the endovascular device (C, 435). In this configuration, the electronic module and the algorithm perform two functions simultaneously: the three standard electrodes (RA, LL, and LL) perform a monitoring function of the heart, while the C electrode (435) allow for recording the ECG at the tip of device.

Figure 4C:
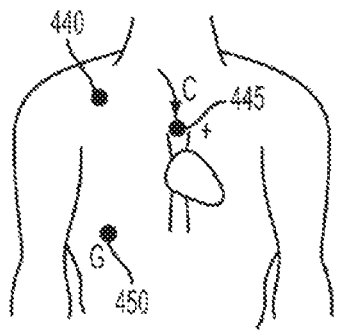

FIG. 4C depicts a telemetry configuration with a single grounded lead, including the configuration illustrated in FIG. 4A and a ground reference (450). This configuration can be used to transmit ECGs remotely through a telemetry system configuration.

Figure 4D:
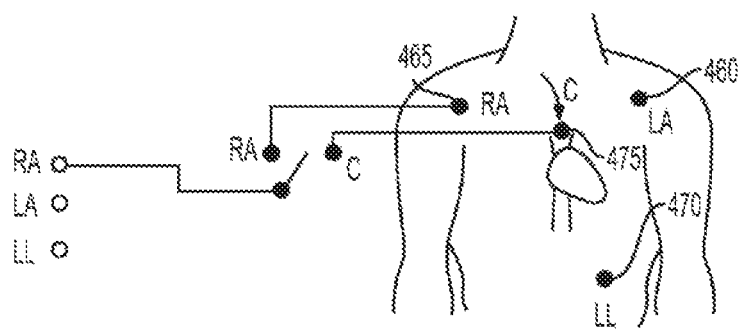

FIG. 4D depicts one use of ECG monitors for guiding endovascular devices. A standard ECG monitor is used having standard inputs RA (465), LA (460), and LL (470). LA (460) is connected to the left arm and LL (470) to the left leg of the patient. The RA input (465) is connected to a switch which can be used be the clinician to switch the RA input (465) between the RA electrode and the catheter (C) electrode 475. Thus either monitoring or guiding of catheter placement can be achieved alternatively.

Figure 5:
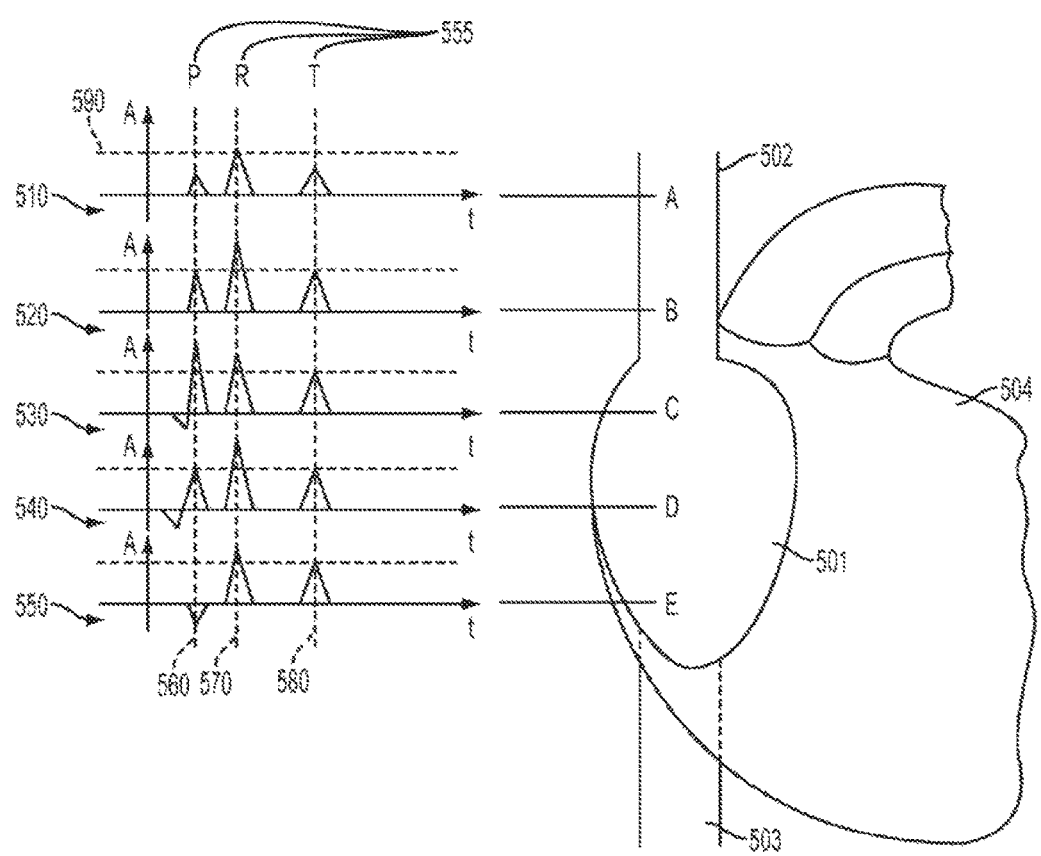
FIG. 5 illustrates exemplary electrocardiogram signal amplitudes at different locations in the central venous system.

FIG. 5 illustrates exemplary electrocardiogram signal amplitudes at different locations in the central venous system.

The heart (504), right atrium (501), superior vena cava (SVC) (502), and the inferior vena cava (IVC) (503) are illustrated. Location A is in the upper SVC, location B is in the lower third of the SVC, location C is at the caval-atrial junction, location D is in the right atrium, and location E is in the upper inferior vena cava.

Graph 510 illustrates an ECG waveform as a function of time at recorded at location A. The absolute amplitude of the waveforms is recorded on an amplitude scale (590). In the case of an endovascular ECG, the standard elements of the electrocardiogram are illustrated: the P-wave (560), the R-wave (570), and the T-wave (580). The amplitudes and shape at location A recorded with a lead configuration as in FIG. 4D are similar to an electrocardiogram recoded at the skin level with the same electrode configuration.

Graph 520 illustrates an endovascular ECG depicted at location B. The amplitude at this location is higher than the one at location A but the overall shapes of the waveform are similar at location A and B.

Graph 530 illustrates an endovascular ECG depicted at location C. At location Cat the caval-atrial junction, the amplitude of the waveform is yet higher than the one at location B and the P-wave has dramatically changed becoming higher than the R-wave. This waveform is an indication of the proximity of the sino-atrial node.

Graph 540 illustrates an endovascular ECG depicted at location D. At location Din the right atrium, the amplitudes are similar to location C but the P-wave changes polarity becoming bi-polar. This is an indication that the measurement of the ECG occurs beyond the sino-atrial node.

Graph 550 illustrates an endovascular ECG depicted at location E. At location E in the inferior vena cava, the waveform is similar to the one at location A in terms of amplitude except the P-wave has reverse polarity. The differences in the ECG waveforms at different locations are used by the algorithms introduced herein to discriminate between the corresponding locations and to assess heart and blood vessel functionality.

Figure 6:
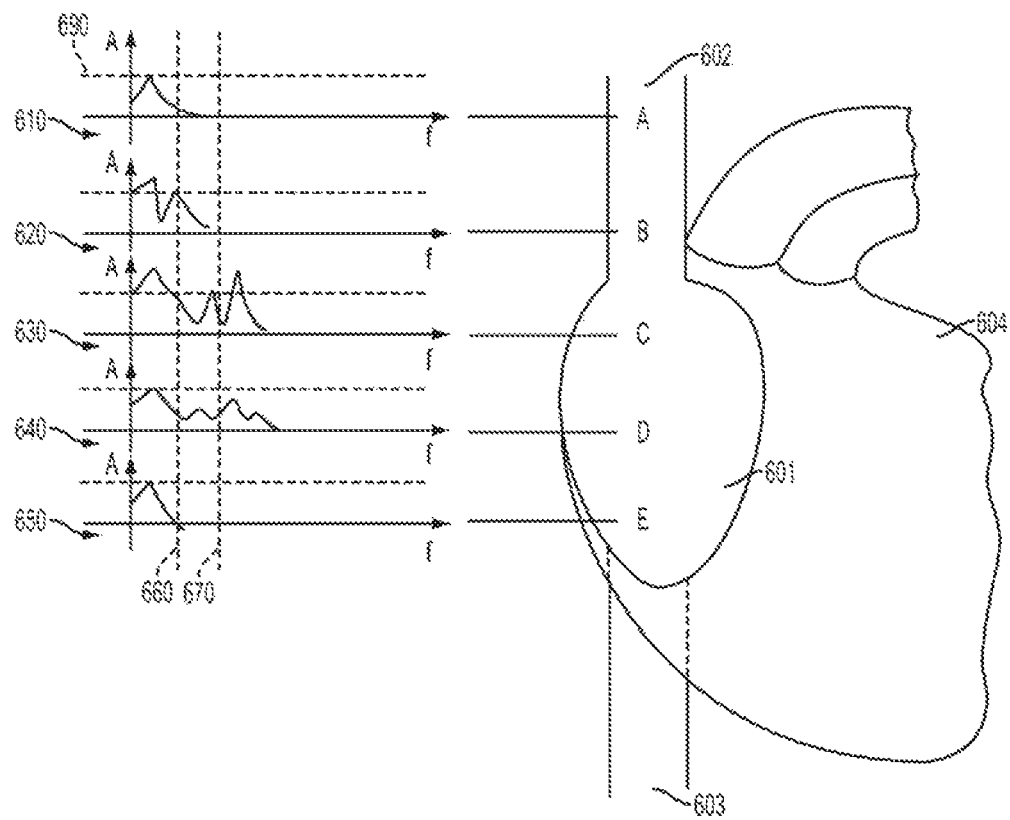
FIG. 6 illustrates exemplary electrocardiogram signal power spectra at different locations in the central venous system.

FIG. 6 illustrates exemplary electrocardiogram signal power spectra at different locations in the central venous system, using a spectral scale (690).

The heart (604), right atrium (601), superior vena cava (SVC) (602), and the inferior vena cava (IVC) (603) are illustrated. Graph 610 illustrates an endovascular ECG spectrum depicted at location A. At location A, the spectrum (610) has the appearance of a single central frequency or single band (660) and with a frequency distribution spectral power and energy similar to those at skin level.

Graph 620 illustrates an endovascular ECG spectrum depicted at location B. At location B the frequency distribution has two major bands and a higher energy and spectral power than the one at location A.

Graph 630 illustrates an endovascular ECG spectrum at location C. At location C, there are multiple (3-4) major frequencies or principal spectral components distributed over a wider range of frequencies (670). This spectral distribution is indicative of the energy distribution around the sino-atrial node. The spectral power and signal energy have increased compared to location B.

Graph 640 illustrates an endovascular ECG spectrum depicted at location D. At location D the spectrum is wider and more broadband indicative of the electrical activity of the right atrium.

Graph 650 illustrates an endovascular ECG spectrum depicted at location E. The frequency spectrum at location E is similar to the one at location A. The differences in the spectral waveforms at different locations are used by the algorithms introduced herein to discriminate between the corresponding locations and to assess heart and blood vessel functionality.

Figure 7:
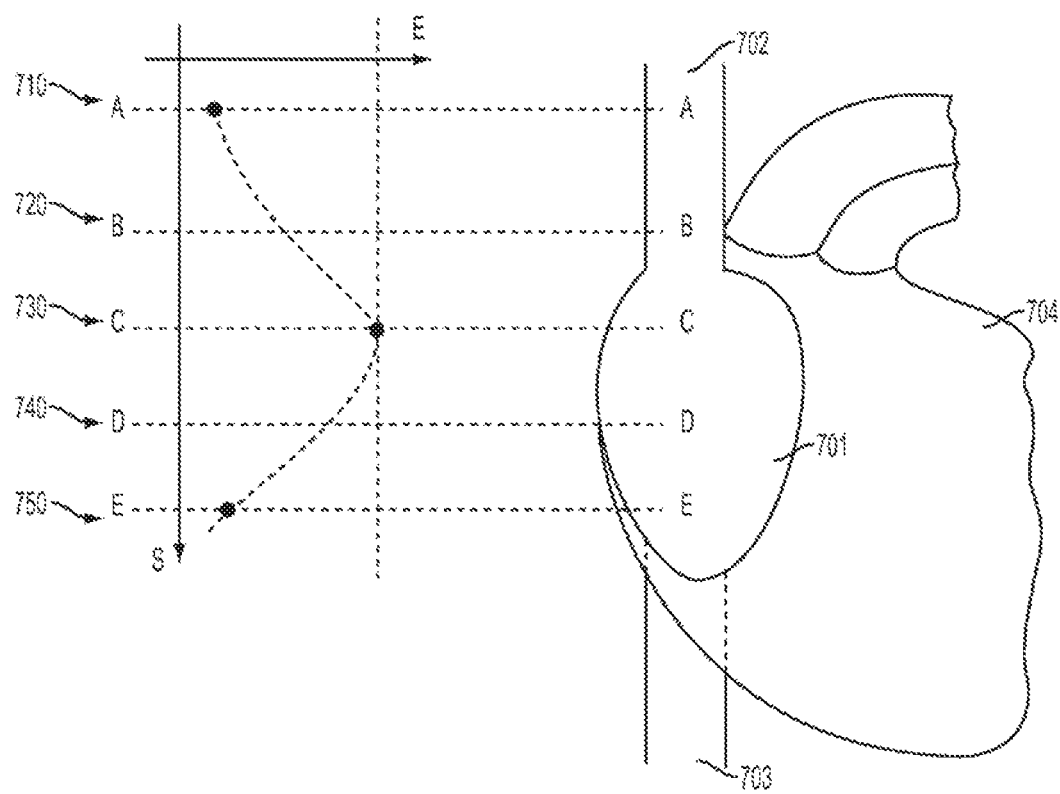
FIG. 7 illustrates exemplary electrocardiogram signal electrical energy distribution at different locations in the central venous system.

FIG. 7 illustrates exemplary electrocardiogram signal electrical energy distribution at different locations in the central venous system. The heart (704), right atrium (701), superior vena cava (SVC) (702), and the inferior vena cava (IVC) (703) are illustrated. Graphs (710, 720, 730, 740, 750) depict the energy distribution at different locations (A, B, C, D and E, respectively) and the changes in time are used by the algorithms introduced herein to discriminate between the corresponding locations and to assess heart and blood vessel functionality.

Figure 16:
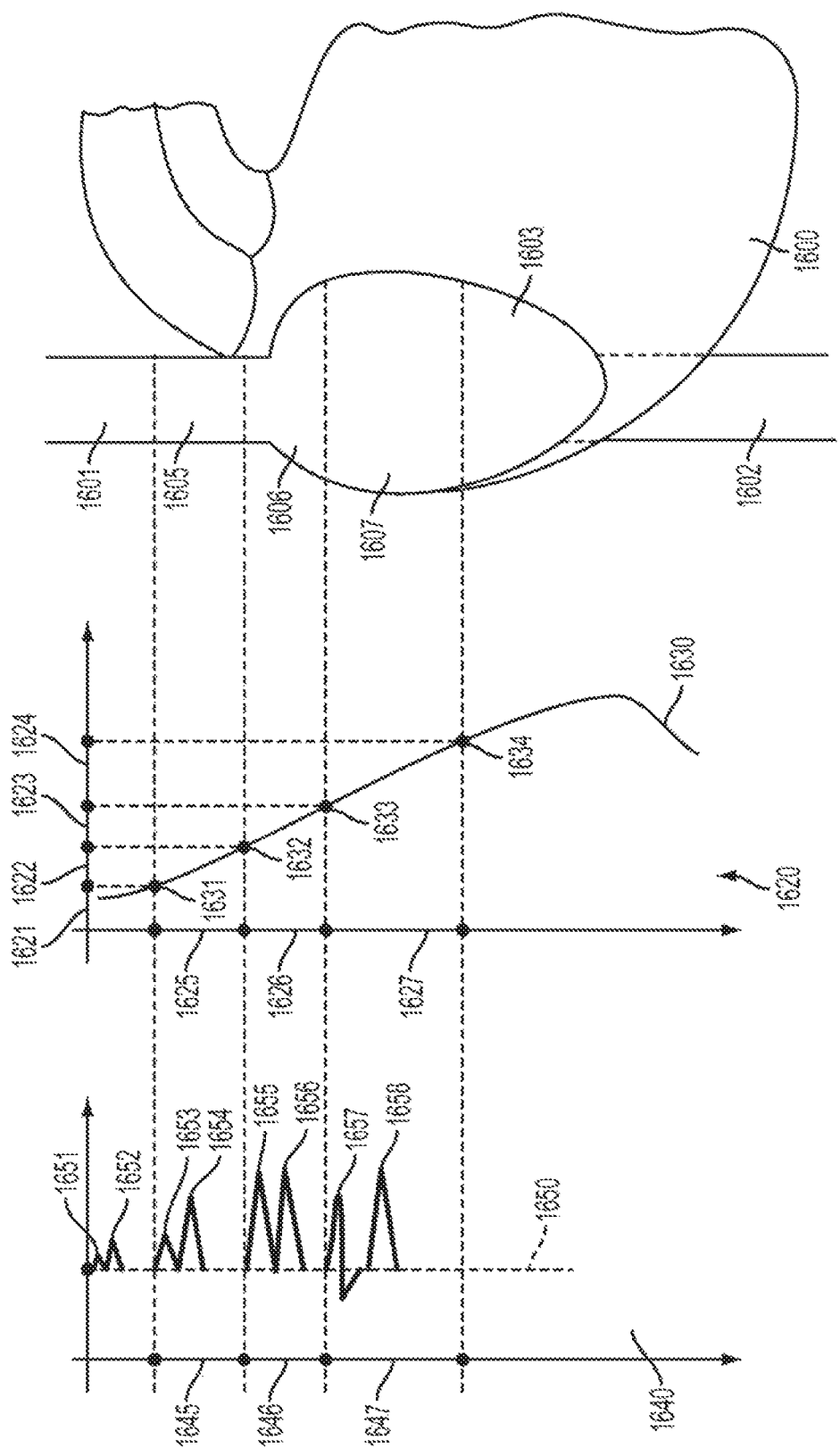
FIG. 16 illustrates a framework for analyzing the endovascular electrography signals, according to an embodiment of the present invention.

Considering FIG. 16 for a moment, a framework for analyzing the endovascular electrography signals according to an embodiment of the present invention is illustrated. The heart is represented by (1600), the superior vena cava by (1601), the inferior vena cava by (1602) and the right atrium by (1603). In this embodiment, there are three regions of interest for placing central venous access devices: the lower third of the superior vena cava or SVC (1605), the caval-atrial junction or CAJ (1606), and the upper right atrium or RA (1607).

The graph (1620) illustrates the electrical energy profile as a function of location in the heart and the graph (1640) illustrates the different electrography waveforms which can be obtained at different locations in the heart. The curve (1630) illustrates the increase of electrical energy detected in each of the regions at the tip of an endovascular catheter advancing from the superior vena cava into the heart. In one embodiment, the energy curve is calculated in time domain, while in another embodiment, the energy curve is calculated in the frequency domain using the frequency spectrum. In one embodiment, the energy is calculated for the actual signal levels, while in another embodiment, the baseline value or other mean values are first subtracted from the signal values before energy calculations. The signal energy or power is calculated in time domain by summing up the squared amplitude values before and/or after baseline subtraction over a determined period of time, e.g., a heartbeat. In the frequency domain, the signal energy or power is calculated by summing up the squared values of the frequency components. In one embodiment, the curve is calculated using the entire electrogram, while in other embodiments, only certain segments of the electrogram are used for the energy calculations, e.g., only the segment corresponding to a "P-wave" of an electrocardiogram. Such a "P-wave" segment is representative of the electrical activity of the sino-atrial node.

Different levels of energy characterize the different locations along the catheter path from the SVC to the heart. These regions can be differentiated in terms of their electrical energy level by using thresholds. Threshold (1631) of energy level defines the beginning of the lower third of the superior vena cava. The energy levels (1621) define the regions in the vasculature of low energy which are distant or further away from the sino-atrial node. The energy levels (1622) between thresholds (1631) and (1632) define the region labeled as the lower third of the superior vena cava (1625 and 1605). The energy levels (1623) between thresholds (1632) and (1633) define the region labeled as the caval-atrial junction (1626 and 1606). The energy levels (1624) between thresholds (1633) and (1634) define the region labeled right atrium (1627 and 1607).

Similarly, the shape and size of the electrogram in graph (1640) relative to a baseline (1650) can be correlated to a location in the heart. Thresholds (1631), (1632), (1633), and (1634) are determined specifically for the type of energy considered for calculations, e.g. the entire electrogram, the P-wave, and/or the S-T segment. Before the lower third of the SVC and corresponding to a relatively low level of energy (1621), the P-wave (1651) and the R-wave (1652) are similar in size and shape with a standard electrocardiogram lead II recorded at the skin level if the right arm standard ECG lead is connected to the catheter and measuring the electrogram signal at the tip of the catheter. In the lower third of the SVC (1605 and 1645), the energy level of the electrogram increases, the electrogram amplitudes increase and the P-wave (1653) increases amplitude and energy relative to the R-wave (1654) to where the P-wave amplitude and energy between half and three quarters of the amplitude and energy of the R-wave. At the caval-atrial junction (1606 and 1646), the energy level of the electrogram increases further, the electrogram amplitudes continue to increase and the P-wave (1655) increases amplitude and energy relative to the R-wave (1656) to where the P-wave amplitude and energy are larger or equal to the amplitude and energy of the R-wave. In the right atrium (1607 and 1647), the energy level of the electrogram increases further, the electrogram amplitudes increase, the P-wave (1657) becomes bipolar and its amplitude and energy relative to the R-wave (1658) start decreasing. These behaviors are quantified, analyzed, and used in order to provide location information regarding the tip of the catheter.

Figure 17:
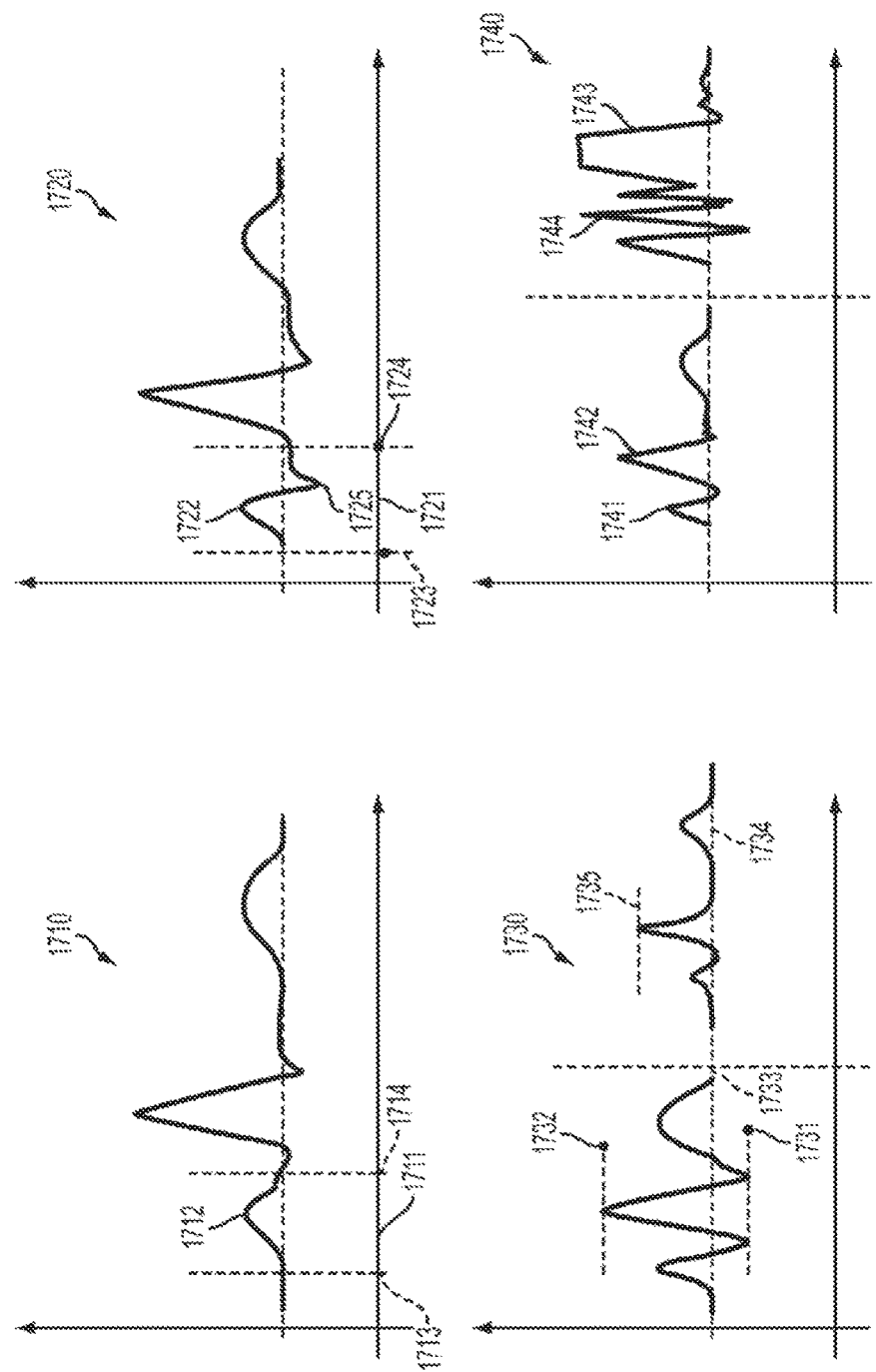
FIG. 17 illustrates several embodiments for electrogram waveform processing.

Considering FIG. 17 for a moment, several electrogram waveform processing embodiments are illustrated. Graphs (1710) and (1720) illustrate a P-wave analysis embodiment. Since the P-wave corresponds to electrical activity of the heart generated by the sino-atrial node, the changes of the P-wave are most relevant with respect to determining the proximity of the sino-atrial node in an endovascular approach. Therefore, in order to assess proximity of the sino-atrial node and location in the vasculature, signal analysis methods in time and frequency domains, as well as signal energy criteria can be applied only to the P-wave segment of an electrogram. In graph (1710), the segment designated for the P-wave analysis (1711) starts at moment (1713) and ends at moment (1714). During the period of time between the starting moment and the ending moment of the P-wave segment, the highest amplitude detected corresponds to the P-wave peak (1712). The starting moment (1713) of the P-wave segment analysis can be determined in a number of ways. In one embodiment, the heart beat is calculated and the R-peak is detected as the maximum amplitude of the heartbeat. Going back from each R-peak a certain percentage of the heartbeat, for example between 20% and 30%, determines the moment when the analysis of the P-wave starts (1713). Going back 2% to 5% of the heart beat from each R-peak determines the end of the segment designated for the P-wave analysis (1714). Similarly, in graph (1720), the designated segment for the P-wave analysis (1721) starts at moment (1723) in the heart cycle and ends at moment (1724). The P-wave in this case is bipolar with a positive maximum amplitude (1722) and a negative maximum amplitude (1725) when compared to the baseline (amplitude equals zero). For the P-waveform defined between the starting point (1713 on graph 1710 and 1723 on graph 1720) and the end point (1714 on graph 1710 and 1724 on graph 1720) time-domain and frequency-domain algorithms are applied according to the present invention.

Graph (1730) illustrates the advantages of baseline subtraction prior to signal energy computation. If the signal energy is calculated in time domain as the sum of the squared signal amplitudes over a heartbeat, then the amplitude variations between levels (1731 and 1732) around baseline (1733) may lead to a lower energy level than the signal with amplitude variations between levels (1734 and 1735) whereby the level (1734) is the baseline. The baseline value (1733) is subtracted from the amplitude values (1731 to 1732) and the baseline value (1734) is subtracted from the amplitude values (1734 to 1735). After subtracting the baseline, the sum of squared amplitude values is calculated. Thus, this sum is proportional to the energy of signal variation around the baseline and therefore it is more appropriate to characterize changes in the signal values/behavior.

Graph (1740) shows a typical electrogram waveform with a P-wave (1741) and an R-wave (1742) and a distorted signal with the P-wave covered by high frequency noise (1744) and the R-wave saturated to a maximum value (1743). In the presence of these kind of artifacts (1744 and 1743) it is very difficult and sometimes impossible to recover the original signal (1741 and 1742). Therefore, according to the present invention, an algorithm is used to detect the presence of artifacts and reduce the amount of artifacts as much as possible. If, after reducing the artifacts, the signal cannot be recovered, then the signal is discarded for the computation of signal energy. The presence of artifacts can be detected in time domain by a high value of the derivative and of its integral, a jump in signal energy, a jump in the value of the baseline or in different averages calculated form the signal. In frequency domain, the artifacts can be detected as a jump in the value of the DC component (frequency zero of the spectrum), as the sudden appearance of high frequency components, and in a jump of the spectral power/energy. In the frequency domain, selective filtering can be applied and all components removed, which are not "typical" for the average behavior of the signal. After selective filtering, the signal is reconstructed in the time domain using an inverse Fourier transform in order to allow for verification of the success of the selective filtering.

Figure 8:
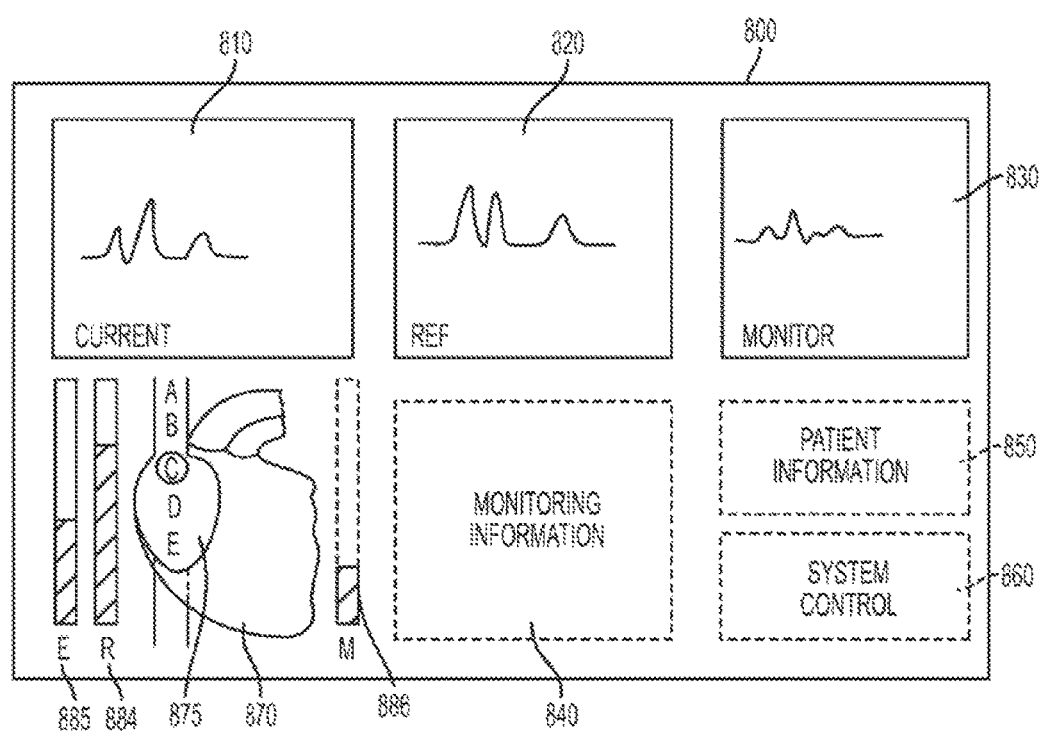
FIG. 8 depicts a graphical user interface according to an embodiment of the present invention.

FIG. 8 depicts a graphical user interface according to an embodiment of the present invention.

Window (810) presents the ECG waveform in real-time as it is acquired by the electronic module using the attached electrode configuration. Window (820) is a reference window and shows a frozen waveform used to compare with the current window. In one embodiment, the reference waveform in window (820) can be obtained through the electrodes connected to the electronic module at a reference location of the catheter and/or using a reference configuration of the skin electrodes. For example, such a reference waveform can be the ECG recorded using an adaptor according to the present invention connected to an endovascular device placed at the caval-atrial junction. In a different embodiment, the reference waveform in window 820 can be a typical waveform at a certain location in the vasculature or of a certain heart condition as it is recorded in a database of waveforms and as it is stored in the storage medium of the computer system. If the electrode configuration allows for simultaneous heart monitoring and recording of electrograms using an endovascular device, window (830) shows one of the standard ECG leads for heart monitoring, while window (810) shows the ECG at the tip of the endovascular devices when connected to an adaptor, such as the ones discussed above.

The icon (870) is a representation of the heart, and the locations A through E (875) illustrate different locations in the heart and vascular system which can be discriminated by analyzing endovascular ECGs in accordance with the methods disclosed herein. As a location in the vasculature is identified by the algorithms, the corresponding place and letter on the icon (875) becomes highlighted or in some other way is made visible to the user. The bars (884), (885), and (886) show signal energy levels. The "E" bar (885) presents the amount of electrical energy computed from the ECG frequency spectrum at the current location of the tip of the endovascular device. The "R" bar (884) presents the amount of electrical energy computed from the ECG frequency spectrum at a reference location. The "M" bar (886) presents amount of electrical energy computed from the ECG frequency spectrum using the monitoring ECG signal from the skin electrodes. The window (840) depicts monitoring information, e.g., heart rate. Patient information (name, date of procedure and others) are shown in window (850). Window (860) contains system control elements like buttons and status information, e.g., scale, scroll speed, system parameters and system diagnostics.

Figure 9:
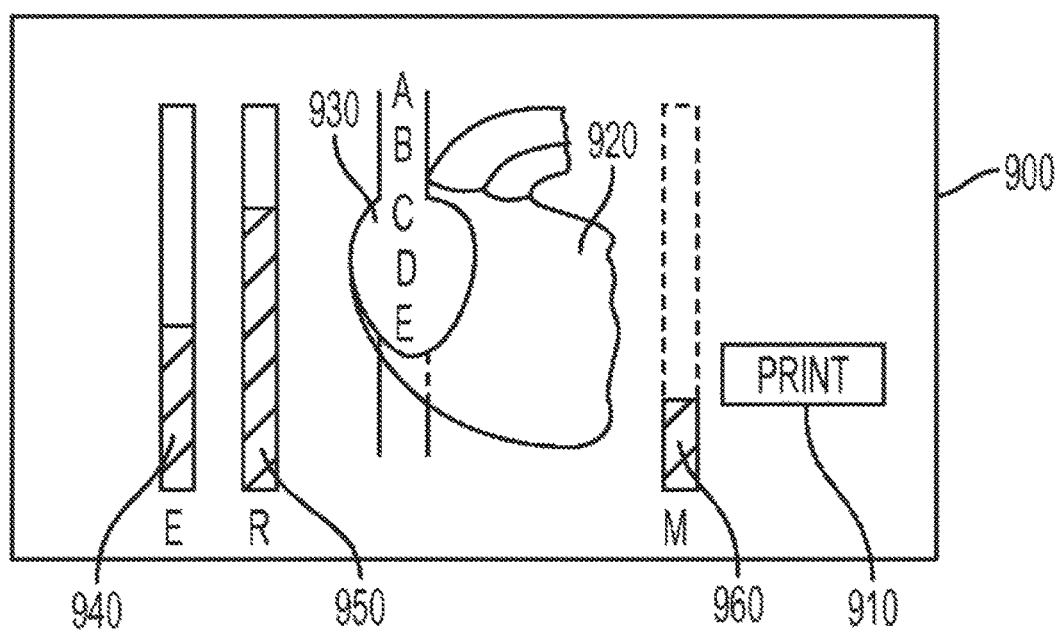
FIG. 9 depicts a graphical user interface according to another embodiment of the present invention.

FIG. 9 depicts a graphical user interface according to another embodiment of the present invention.

The icon (920) is a representation of the heart and the locations A through E (930) illustrate different locations in the heart and vascular system which can be discriminated by analyzing endovascular ECGs. As a location in the vasculature is identified by the algorithms, the corresponding place and letter on the icon (930) becomes highlighted or in some other way is made visible to the user. The bars (940), (950), and (960) show signal energy levels. The "E" bar (940) depicts the amount of electrical energy computed from the ECG frequency spectrum at the current location of the tip of the endovascular device. The "R" bar (950) shows the amount of electrical energy computed from the ECG frequency spectrum at a reference location. The "M" bar (960) shows amount of electrical energy computed from the ECG frequency spectrum using the monitoring ECG signal coming from the skin electrodes. The button "Print" (960) allows the user to print the information documenting the case on a printer, for example on a label printer for quick attachment to the patient's chart.

Figure 10A:
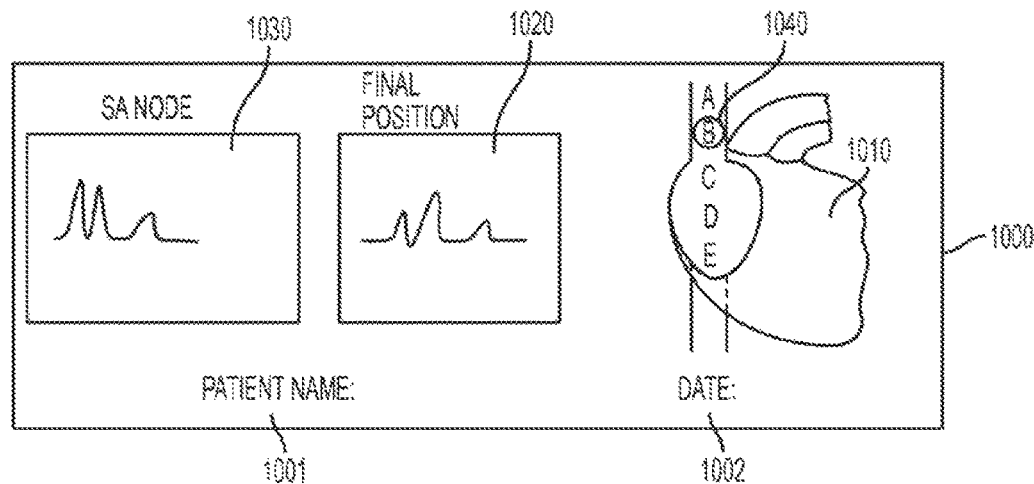
FIGS. 10A and 10B depict an exemplary printouts for the information displayed by the graphical user interface, according to an embodiment of the present invention.
Figure 10B:
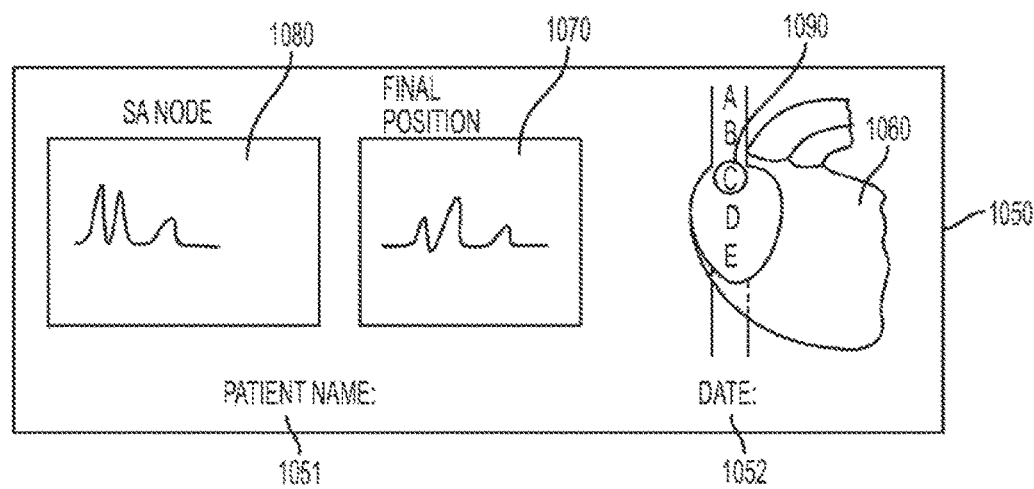

FIGS. 10A and 10B depict an exemplary printouts for the information displayed by the graphical user interface, according to an embodiment of the present invention.

FIG. 10A illustrates a printout (1000) for the case of a catheter tip placement procedure in the lower third of the SVC. The field 1010 depicts the heart icon whereby the letter "B" corresponding to the lower third of the superior vena cava (SVC) is highlighted (1040). Field 1030 depicts the reference ECG waveform recorded at the tip of the catheter at the caval-atrial junction in the proximity of the sino-atrial node. Field 1020 depicts the ECG waveform at the tip of the catheter in the position in which it was placed at the end of the procedure. For FIG. 10A, this location is in the lower third of the SVC and the ECG waveform corresponds to this location. The patient name (1001) and the date of procedure (1002) are also printed.

FIG. 10B depicts a similar printout (1050) except that the final position at the end of the procedure is at the caval-atrial junction at location C (1090) on the heart icon (1060). The "SA Node" field depicts the reference ECG waveform (1080), and the "Final Position" field (1070) shows that the catheter was placed with the tip at the sino-atrial node: the ECG waveform in final location is similar or even identical with the one in the reference location at the sino-atrial node (SA Node). It is known that the proximity of the SA Node indicates a location at the caval-atrial junction. These locations are sometimes considered identical by some clinicians.

Figure 11:
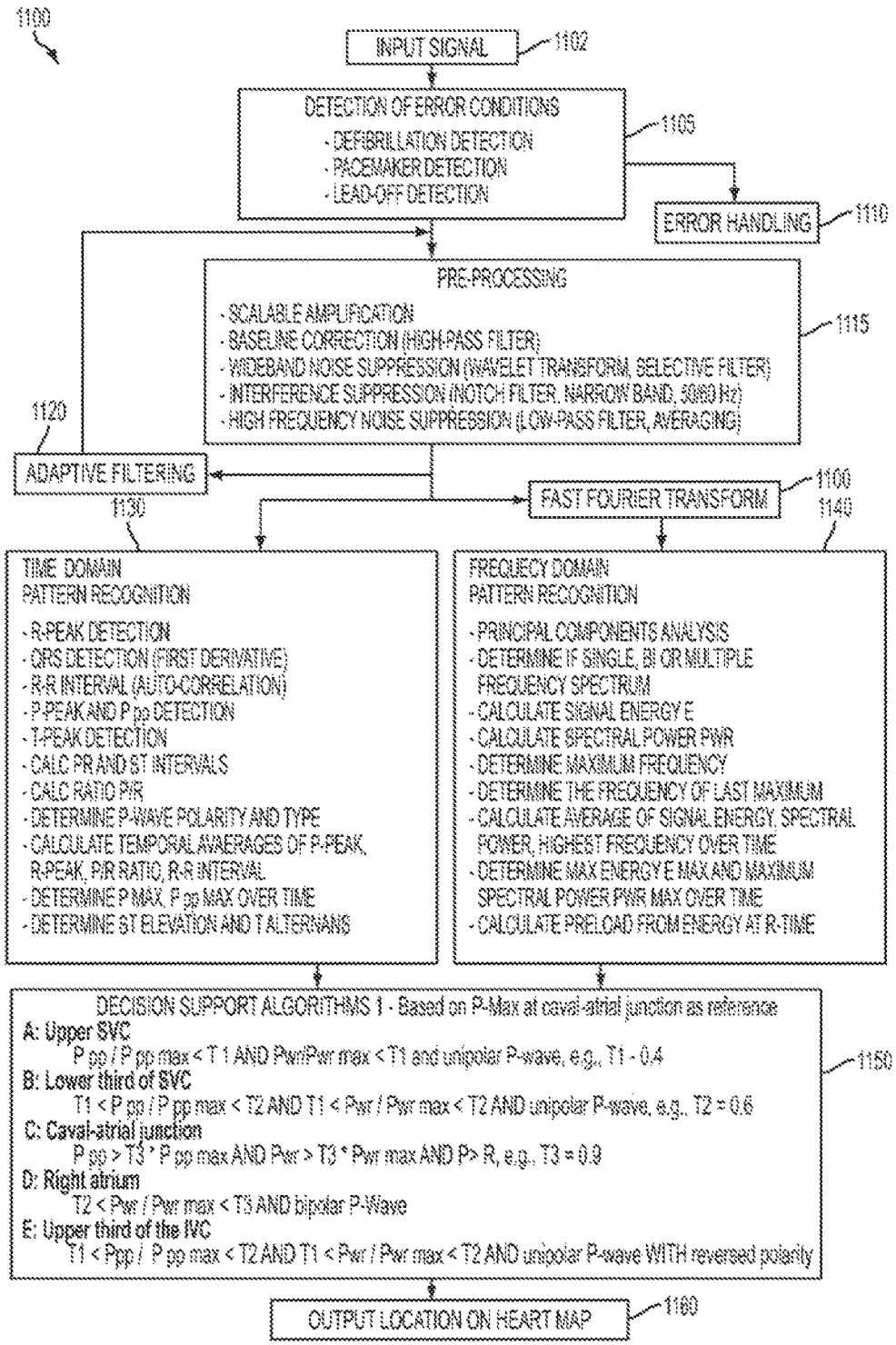
FIG. 11 is a block diagram for a computer-based method for positioning an endovascular device in or near the heart using electrocardiogram signals.

FIG. 11 is a block diagram for a computer-based method (1100) for positioning an endovascular device in or near the heart using electrocardiogram signals.

The algorithms are applied to the input signal (1102) (ECG) acquired by the adaptor to the endovascular devices and, optionally, through skin electrodes as well. The Error Detection Block (1105) detects at least three types of error conditions/exceptions, such as, for example, when a defibrillator has been applied to the patient, when a pacemaker is firing excitation pulses and/or when a lead/electrode is off. These errors/exceptions may be handled differently, and the user may be informed about the presence of an exception and the way of handling the exception (1110).

The Pre-Processing block (1115) may amplify the signal, reduce noise, eliminate artifacts, etc. In one embodiment, rescaling the signal to the display range occurs under user control and is not automatic, as with most currently available ECG monitors. Thus, changes in the amplitude of the ECGs are easily noticed. A high-pass filter corrects the baseline and reduces such artifacts as respiratory artifact. Wideband noise suppression may be achieved using a selective filter, e.g., a wavelet transform. Electromagnetic interference with other equipment and the power grid may be suppressed by a notch filter (narrow band filter) centered at 60 Hz or 50 Hz to accommodate domestic or international power supplies. High frequency noise may be suppressed with a low-pass filter, which, in one embodiment, is implemented with variable length averaging, such as, for example, a running window corresponding to a heart cycle, an averaging of the ECG over several consecutive heart cycles, etc. The Adaptive Filtering block (1120) optimizes the filter coefficients by minimizing an error signal.

The Time-Domain Pattern Recognition block (1130) identifies elements of the ECG waveform, their relationship(s) and their behavior(s) in time. An important aspect of the time-domain pattern recognition algorithm in block 1130, as well as of the Frequency Domain Patter Recognition block 1140, is data history. The ECGs are analyzed in real time for certain elements, and, for other elements, a data buffer with an appropriate buffer length is maintained in the memory of the electronic and/or computer modules in order to allow for historic data analysis and prediction based on this analysis. In one embodiment, the data history buffer is several seconds long allowing for the ECG signal corresponding to several heartbeats to be saved in the buffer. A double buffering technique allows the waveform in one buffer to be processed while the second buffer continues to store signals. Thus no signal data are lost while the waveform in one buffer is processed. After data processing on one buffer is completed, the results are sent to the Decision Support Algorithms (1150) and the two buffers switch roles. The length of the buffer accommodates the time duration of data processing in order to ensure that no data are lost. A similar double buffering technique is also applied to the data subject to Frequency Domain Pattern Recognition block (1140).

In the case of an endovascular ECG, elements of interest may include, but are not limited to, one or more of the following:

1. The P, Q, R, S, T, and U waves, their peaks, amplitudes and duration;
2. The duration of the P-R, S-T, and T-P segments/intervals;
3. The elevation of the S-T segment;
4. The variances of the P-P and R-R intervals;
5. The variance of the S-T and of the R-T intervals, etc.;
6. The peak-to-peak values of the P-wave and of the QRS complex;
7. The ratio of the P-wave and R-wave amplitudes and the ratio of the P-wave and QRS complex peak-to-peak amplitudes;
8. The polarity of the P-wave: single positive, single negative, or bipolarity;
9. The derivative of the P-wave, QRS-complex, and T-wave;
10. Temporal average of the R-R interval and the heart beat;
11. Maximum value of the P-wave amplitude/peak and of the P-wave peak-to-peak amplitude over a certain period of time;
12. Maximum value of the R-wave amplitude/peak and of the ORS complex peak-to-peak amplitude over a certain period of time.

Several techniques may be used to derive the information listed above from the ECG waveforms, including, but not limited to, one or more of the following:

1. "Peak detection";
2. Computation of first derivatives;
3. Running averages along the signal in one heartbeat and along multiple heartbeats;
4. Adaptive thresholding;
5. Auto-correlation.

The Fast Fourier Transform in block (1125) performs a Fast Fourier Transform on a number of ECG samples stored in a buffer of a certain length, e.g., 256, 512, 1024, 2048 or more data samples. The Fourier Transform transforms the waveform from the time domain into the frequency domain.

The Frequency-Domain Pattern Recognition block (1140) illustrates various aspects of pattern recognition performed on the ECGs in the frequency domain, including, but not limited to, one or more of the following:

1. Principal components analysis, i.e., determination of the most significant elements of the frequency spectrum (similarly to determining the morphological elements of the electrograms, e.g., certain waves and segments in time domain);
2. Data compression in order to reduce the amount of computation based on the principal components;
3. Determination of the number and morphology of the principal components, in particular determination if the spectrum has only one, two or multiple main frequencies (frequency bands);
4. Calculation of the spectral power and of the signal energy from the frequency spectrum;
5. Running average along the frequency dimension over a single spectrum in order to reduce wideband noise;
6. Running average along several spectra in order to filter out artifacts;
7. Determination of additional morphological elements of the spectrum, e.g., the maximum frequency, the energy contained in the maximum frequency, the frequency histogram, i.e., what frequencies contain how much energy, the frequency of the highest significant maximum energy peak, etc.;
8. Calculation of behavior and averages over time of the principal components and other parameters determined from the spectral distribution, e.g., determining the maximum value of the signal energy and of the spectral power over a certain period of time;
9. Determine/estimate certain heart conditions based on the spectral analysis. This determination/estimation is also performed in more detailed in the decision support blocks 1150 and 1250.

Several decision support algorithms use the information provided by the time domain pattern recognition and frequency-domain pattern recognition algorithms. In one embodiment, block (1150) supports placing an endovascular device in either the lower third of the SVC or at the caval-atrial junction.

In particular, block 1150 is based on the concept of first reaching the caval-atrial junction during catheter placement. At the caval-atrial junction or near the sino-atrial node the P-wave and other electrical parameters reach a maximum value. At the caval-atrial junction the P-wave is unipolar. After reaching the sino-atrial node at the caval-atrial junction, i.e., the maximum value of the P-peak amplitude and spectral power, the catheter is pulled back several centimeters until the P-wave decreases to half the amplitude reached at the caval-atrial junction. At the location where the P-wave has decreased to half the amplitude as the caval-atrial junction, the catheter is considered to be in the lower third of the superior vena cava. The P-wave peak amplitude or peak-to peak amplitude, as well as the spectral power, is used to map the location in the vasculature to the ECG waveform.

More particularly, after receiving an endovascular ECG signal associated with an endovascular device, the signal is processed, over a plurality of predetermined time periods, to calculate a P-wave amplitude and a spectral power for each predetermined time period. A maximum P-wave amplitude is then determined from the plurality of P-wave amplitudes, as well as an associated maximum spectral power from the plurality of spectral powers. The location at which these maximum values are determined is associated with a predetermined location in or near the heart, such as the cava-atrial junction. The location of the endovascular device is then calculated, for each predetermined time period, based on a ratio of the P-wave amplitude to the maximum P-wave amplitude and a ratio of the spectral power to the maximum spectral power, and the location of the endovascular device is then displayed to the user. Additionally, the polarity of the P-wave and the R-wave amplitude may also be used to determine the location of the endovascular device.

A single criterion or a combination of such criteria can be used to support decision making. In one embodiment, T1, T2, and T3 may be empirically established thresholds which are different for each patient, and the algorithm can use an adaptive loop to adjust the thresholds based on the current measurements. In another embodiment, these thresholds are predetermined.

In alternative embodiments, the ratio between the P-peak/P amplitude or the P-wave peak-to-peak amplitude to the R-peak/R amplitude or to the QRS complex peak-topeak amplitude can also be used to establish location relative to the sino-atrial node. In one embodiment the P-peak/amplitude must be approximately half of the R-peak/amplitude and the P-wave must be unipolar for the location to correspond to the lower third of the SVC. In another embodiment, the P-wave peak-to-peak must be half of the QRS peak-to-peak amplitude and the P-wave must be unipolar for the location to correspond to the lower third of the SVC.

As discussed above, the results of the decision support algorithms block 1150 may be presented to the user, for example, by high lightening the appropriate location on the heart icon corresponding to the type of ECG identified by the system (1160).

Figure 12:
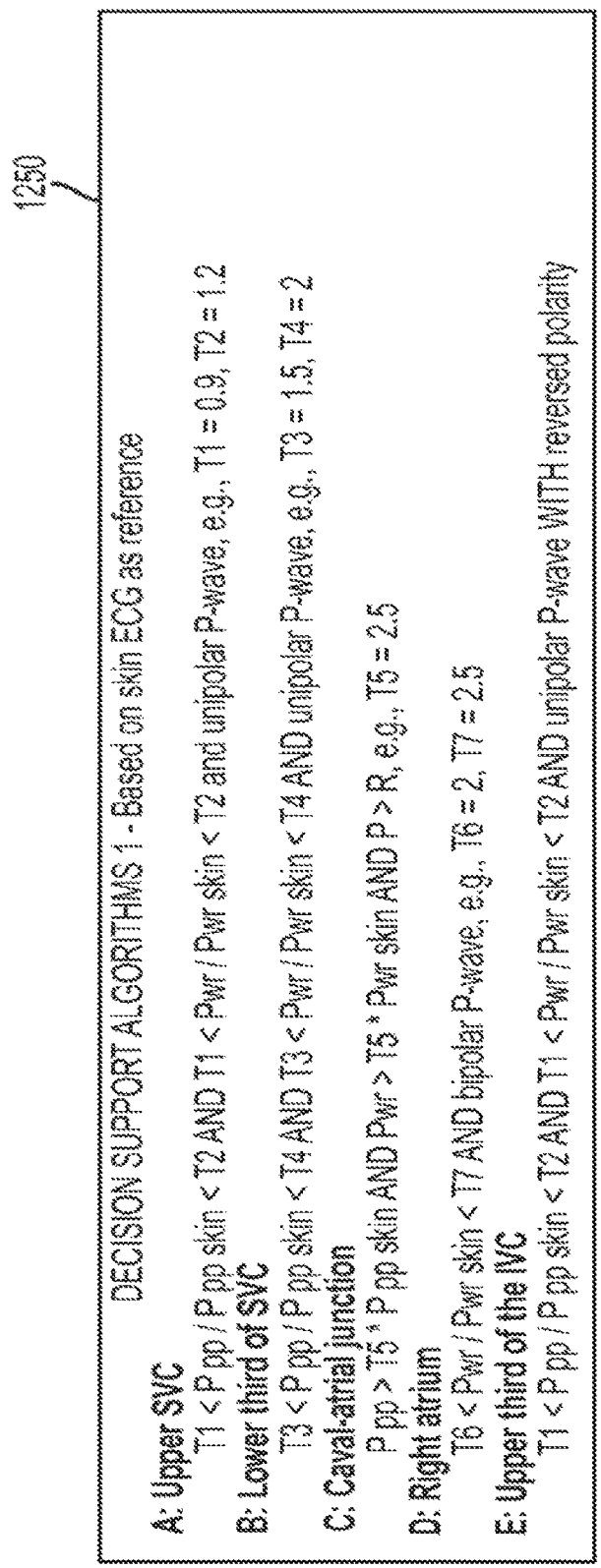
FIG. 12 illustrates another decision support algorithm for a computer-based method for positioning an endovascular device in or near the heart using electrocardiogram signals, according to an alternative embodiment.

The decision support algorithm block 1250, depicted in FIG. 12, is based on comparing the P-wave, R-wave and P-wave spectral power at the current locations with the values of these parameters determined from the skin electrocardiograms in an equivalent lead, e.g., lead II. Thresholds T1 through T6 are empirical values subject to adaptive adjustments relative to each patient. Each of the criteria or a combination of criteria shown in FIG. 12 can be used.

Other decision algorithms can also be used, in particular related to the level of electrical energy as calculated from the ECG spectrum. In the case of placing endovascular devices, one criterion may be that, at the location corresponding to the lower third of the SVC, the average electrical energy calculated from the endovascular ECG is twice as high as the average electrical energy calculated from the endovascular ECG at skin level or from a skin ECG in a corresponding lead, e.g., lead II.

Method for Placement of Central Venous Catheters

A method of placing a central venous catheter (CVC) is presented below.

1. Estimate or measure the required length of the vascular access device (CVC) for the given patient.
2. If using saline and adaptor (200), go to step 11; if not, proceed as follows. Insert a guidewire into the CVC and flush align the guidewire tip and the catheter tip. Measure the length of the guidewire outside the CVC. This measurement is necessary in order to be able to realign the tip of the catheter and of the guidewire after inserting the guidewire in the vasculature. After taking the measurement, for example with sterile measuring tape or with surgical thread, remove the guidewire from the CVC.
3. Gain vascular access and insert the guidewire for the estimated required length.
4. Insert the CVC over the wire such as to leave outside the CVC the length of the guidewire measured at step 1. Thus the CVC inserted over the wire and the guidewire tip are flush aligned.
5. Connect a sterile electrical adaptor to the guidewire per the instructions for use.
6. Connect the other end of the sterile electrical adapter to the ECG cable of the electrography system.
7. Check that the display of the electrography system indicates desired position of the catheter tip per the instructions for use of the electrography system: in the lower third of the SVC, at the caval-atrial junction or in the right atrium. Typically, the location of the tip of the catheter will be identifiable through the specific shape of the P-wave and of the P-wave relative to the R-wave of the electrogram and/or by the energy levels and thresholds.
8. Adjust the position of the guidewire and CVC by pulling and/or pushing them together as not to change the flush alignment until the ECG waveform on the screen indicates that the desired position has been reached. Correlate the actual inserted length with the estimated length.
9. After the position has been reached, disconnect the electrical adaptor and remove the guidewire.
10. Secure the CVC in location.
11. Continue here if saline and adaptor (200) are used.
12. Gain vascular access and introduce the CVC over the guidewire as currently specified by the existing protocols.
13. Remove the guidewire.
14. Attach the sterile adaptor (200) to the CVC.
15. Attach the electrical connection (234) of the adaptor (200) to the ECG cable of the electrography system.
16. Fill a syringe with saline and connect it to the other end of the adaptor (200). Flush the catheter lumen with saline as to create a conductive saline column all way through the catheter tip.
17. Check that the ECG waveform shown on the display of the electrography system indicates desired position of the catheter tip per the instructions for use of the electrography system: in the lower third of the SVC, at the caval-atrial junction or in the right atrium. Typically, the location of the tip of the catheter will be identifiable through the specific shape of the P-wave and of the P-wave relative to the R-wave of the electrogram and/or by energy levels and thresholds.
18. Adjust the position of the CVC by pulling and/or pushing until the ECG waveform on the screen indicates that the desired position has been reached. Correlate the actual length with the estimated length.
19. After the desired position has been reached remove the syringe and the adaptor (200).
20. Secure the catheter.

Method for Placement of Implantable Ports

A method of placing the catheter piece of an implantable port is similar to the method for placing a CVC. The adaptor (200) should be connected to the catheter of the implantable port, and the syringe with saline must be connected to the other end of the universal adaptor. A different electrical adaptor should be connected to a syringe needle placed in the catheter of the implantable port. After reaching the desire position, the catheter should be connected to the implantable port. Method for Placement of Peripherally Inserted Central Catheters Open and Closed Ended Both open-ended and closed-ended peripherally inserted central catheters (PICC) can be placed as described herein, and the method of PICC placement is similar to the one of placing CVCs. The inventive steering mechanism described herein can be used to bend the tip of the PICC in case the catheter fails to advance in the desired direction.

Method for Placement of Hemodialysis Catheters

A method for placing hemodialysis catheters is similar to the method introduced herein for placing CVCs. The inventive steering mechanism described herein can be used to bend the tip of the hemodialysis catheter in case the catheter fails to advance in the desired direction. Two different guidewires with adaptors (220) can be used for each of the lumens of the hemodialysis catheter as to guide placement of one lumen into the right atrium and of the other lumen at the caval-atrial junction using the electrography system. Each of the lumens of the hemodialysis catheter can be placed independently in sequence or at the same time by connecting the adaptors (220) of each of the lumens with different electrodes of the ECG cable of the electrograph system.

Method for Placing Central Venous Access Devices in Patients with Arrhythmias

Traditionally, patients with arrhythmias have been excluded from procedures of guiding central venous lines placement using the endovascular ECG method because of the lack of visible changes in the shape of the P-wave. The energy criteria for the P-wave analysis described herein can be used to guide the placement of central venous access devices in patients with arrhythmias. In arrhythmia patients, the electrical signals generated by the sino-atrial node have a certain degree of randomness, such that they are not synchronized in order to produce a consistent P-wave. Nevertheless, as previous studies have shown, the electrical activity of the sino-atrial node exists and generates electrical energy of intensities typical to the proximity of the sino-atrial node. In one embodiment, the algorithm uses the energy as measured from the endovascular electrogram in order to map certain location in the vasculature. As such, this algorithm can be used to guide placement in patients with arrhythmias when only the electrical energy is indicative of location but not the shape of the P-wave.

Method for Monitoring Tip Location and Certain Aspects of the Electrical Activity of the Heart Certain aspects of the electrical activity of the heart can be monitored continuously or intermittently using the devices introduced herein. Either an electrical adaptor or adaptor (200) connected to the electrography system can be used for monitoring. The electrical adaptor can be connected to any stylet or other conductive member introduced in any venous access device or in any arterial device. Adapter (200) can also be connected to any venous or arterial line as long as the infusion of a conductive solution, e.g., saline is possible. Adapter (200) can also be used when electrically conductive fluids are inserted in the body using an infusion pump. Monitoring the tip location and/or certain aspects of the electrical activity of the heart can be performed in a number of clinical situations.

1. Adaptor (200) can be attached to a number of central venous devices post insertion, e.g., at bedside and/or in home care situations: PICCs, CVC, hemodialysis catheters. By connecting the adapter to such a catheter and to an electrography system according to the present invention and by injecting saline into the catheter, the location of the tip of the catheter can be confirmed and/or certain electrically activity of the heart can be monitored during the time the adapter is connected by using methods similar to those introduced above in the present inventions.
2. Adaptor (200) can be connected to an arterial line between the arterial line and the other devices connected to the arterial line. The blood present in the arterial line and in the universal adaptor ensures the electrical connection between the blood and the electrography system. Thus the electrical activity of the heart can be continuously monitored. This is particularly important in the case of monitoring the preload changes which translate in changes of the electrical energy of the heart during the S-T segment of the ECG waveform.
3. Monitoring of the tip location and of the electrical activity of the heart can also be achieved by using the electrography system and connecting the adaptor (200) between a central venous line and a pressure measuring system while performing central venous pressure measurements.
4. In the case of an implanted port, a needle can be inserted into the port chamber and the catheter can be flushed with saline using a syringe filled with saline. An electrical adaptor can be attached to the needle and to the electrography system. The detected electrogram signal will contain information from the skin level where the needle is in contact with the skin and from the tip of the catheter through the injected saline column. Since the impedance of the path to the catheter tip is lower than the one to the skin, the detected signal contains both components, i.e., at the skin level and at the tip of the catheter. By subtracting the skin level signal, the signal at the tip of the catheter can be estimated and thus the tip position and certain electrical activity of the heart according to the algorithms described in the present invention.

Figure 13:
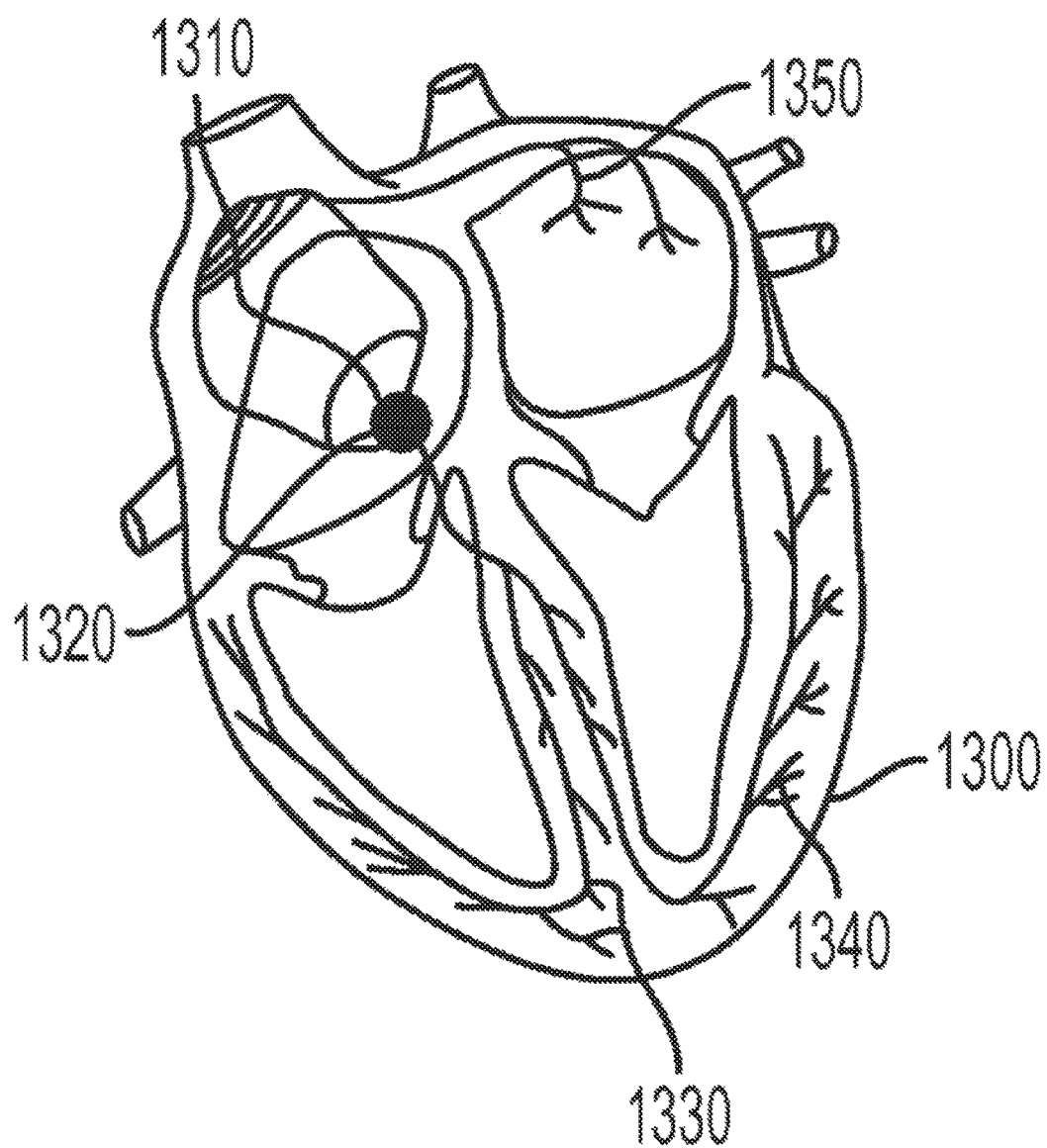
FIG. 13 illustrates the cardiac conduction system of the heart.
Figure 14:
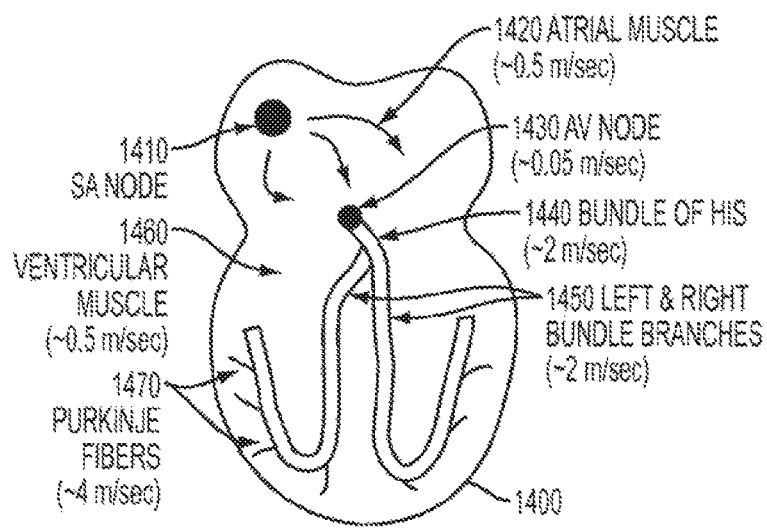
FIG. 14 illustrates electrical signal propagation in the conduction system of the heart.

FIG. 13 illustrates the cardiac conduction system of the heart, while FIG. 14 illustrates electrical signal propagation in the conduction system of the heart.

These figures illustrate the conductive mechanism of the heart, which explains why the electrical energy distribution within the heart as measured is indicative of specific locations within the heart. Accordingly, local electrical signals, behaviors and energy concentrations can be measured and locations within the heart and blood vessel can be determined more accurately; local heart conditions can also be described more accurately.

The conduction system of the heart begins with the heart's dominant pacemaker, the sino-atrial node (1310). The intrinsic rate of the SA node is 60 to 100 beats/minute. When an impulse leaves the SA node, it travels through the atria along the Bachmann's bundle (1350) and the inter-nodal pathways, on its way to the atrioventricular (AV) node (1320) and ventricles. After the impulse passes through the AV node, it travels to the ventricles, first down to the bundle of His (1330) then along the bundle branches and finally down to the Purkinje fibers (1340). Pacemaker cells in the junctional tissue and Purkinje fibers on the ventricles normally remain dormant because they receive impulses from the SA node. They initiate an impulse only they do not receive one from the SA node. The intrinsic rate of the AV junction is 40 to 60 beats/minute, the intrinsic rate of the ventricles 20 to 40 beats/minute. The different propagation speeds of the electrical impulses are shown in FIG. 14. From the SA node (1410) the impulses propagate through the atrial muscle (1420) and through the ventricular muscle (1460) at app. 0.5 ms, through the bundle branches (1440) and (1450) at app. 2 m/sec, through the Purkinje fibers (1470) at app 4 m/s and through the AV node (1430) at app. 0.05 m/s.

The electrical signals and the electrical energy distribution are advantageously used to identify the proximity of the sino-atrial node and right atrial electrical activity even in the cases of arrhythmia, i.e., in the absence of a coherent P-wave measured by standard skin electrocardiogram. While in some cases of arrhythmia random electrical signal generated in the right atrium is not coherent enough to propagate through the body to the skin, the electrical energy is still present in the right atrium and can be detected by local endovascular measurements as a non-coherent P-wave, i.e., as significant electrical activity in the P-segment of the ECG waveform. Energy measurements are also less sensitive to some local abnormalities in impulse conduction: altered automaticity (arrhythmias), retrograde conduction of impulses, reentry abnormalities.

The electrical signals and the electrical energy distribution are also advantageously used to quantify heart functionality, e.g., preload which is related to the depolarization and extension of the heart muscle.

The electrical signals and the electrical energy distribution are also advantageously used to guide guidewires and guiding catheters through the aorta into the left heart. This method is useful in simplifying the access to the left atrium and to the coronary arteries and in reducing the amount of contrast and radiation needed to guide endovascular devices to those locations. In a different application, the inventive apparatus can also be used to guide catheters, e.g. Swan-Ganz through the right ventricle into the pulmonary artery. Other endovascular devices can be guided and be used to measure endovascular electrical activity in other locations of the cardiovascular system which are identifiable by the cardiograms measured with the new apparatus introduced in the present invention.

Figure 15:
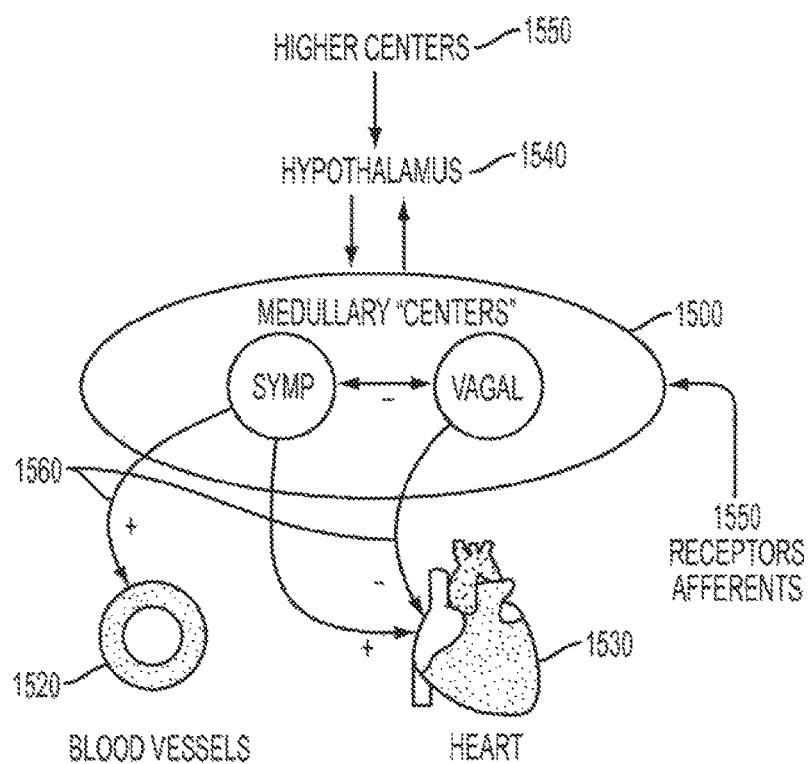
FIG. 15 illustrates electrical activity in the cardiovascular system due to neuronal control system.

FIG. 15 illustrates electrical activity in the cardiovascular system due to neuronal control system. Several paths of conduction are related to the mechanism of control of heart (1530) and blood vessel (1520) activity: receptors (1510), e.g., pressure receptors transmit information related to the state of the blood vessels and to the state of the heart to the nervous system through the Medullary centers (1500). The hypothalamus (1540) and the higher centers (1550) are involved in processing and reacting to the information received from the sensors/receptors. In turn they send impulses (1560) back to blood vessels and the heart. By measuring electrical activity related to the control system, information regarding heart conditions can be obtained which could not have been obtained previously.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

What is claimed is:

1. A computer-based method for positioning an endovascular device in or near a heart using electrocardiogram (ECG) signals, comprising:
   receiving an endovascular ECG signal, associated with the endovascular device, including a plurality of waveforms, each waveform having at least a P-wave component;
   processing the endovascular ECG signal, over a plurality of predetermined time periods, to calculate a P-wave amplitude and a spectral power for each predetermined time period;
   determining a maximum P-wave amplitude from a plurality of P-wave amplitudes resulting from processing the endovascular ECG signal over the plurality of predetermined time periods, and an associated maximum spectral power from a plurality of spectral powers resulting from processing the endovascular ECG signal over the plurality of predetermined time periods;
   associating the maximum P-wave amplitude and the maximum spectral power with a predetermined location in or near the heart;
   calculating a location of the endovascular device, for each predetermined time period, based on a ratio of the P-wave amplitude to the maximum P-wave amplitude and a ratio of the spectral power to the maximum spectral power; and
   displaying the location of the endovascular device to a user for each predetermined time period.

2. The computer-based method according to claim 1, wherein the P-wave amplitude for each predetermined time period is a peak-to-peak value, and the maximum P-wave amplitude is a peak-to-peak value.

3. The computer-based method according to claim 2, wherein processing the endovascular ECG signal includes determining a polarity for each P-wave amplitude, for each predetermined time period, and calculating the location of the endovascular device is also based on the P-wave polarity for each predetermined time period.

4. The computer-based method according to claim 3, wherein the predetermined location is a caval-atrial junction.

5. The computer-based method according to claim 4, wherein the location of the endovascular device is an upper portion of a superior vena cava if the ratio of the P-wave amplitude to the maximum P-wave amplitude is less than 0.4, the ratio of the spectral power to the maximum spectral power is less than 0.4, and the P-wave polarity is unipolar.

6. The computer-based method according to claim 5, wherein the location of the endovascular device is a lower third of the superior vena cava if the ratio of the P-wave amplitude to the maximum P-wave amplitude is between 0.4 and 0.6, the ratio of the spectral power to the maximum spectral power is between 0.4 and 0.6, and the P-wave polarity is unipolar.

7. The computer-based method according to claim 6, further comprising: calculating an R-wave amplitude for each predetermined time period when processing the endovascular ECG signal, wherein the location of the endovascular device is the caval-atrial junction if the ratio of the P-wave amplitude to the maximum P-wave amplitude is greater than 0.9, the ratio of the spectral power to the maximum spectral power is greater than 0.9, and the P-wave amplitude is greater than the R-wave amplitude.

8. The computer-based method according to claim 7, wherein the location of the endovascular device is a right atrium if the ratio of the spectral power to the maximum spectral power is between 0.6 and 0.9, and the P-wave polarity is bipolar.

9. The computer-based method according to claim 8, wherein the location of the endovascular device is an upper third of an inferior vena cava if the ratio of the P-wave amplitude to the maximum P-wave amplitude is between 0.4 and 0.6, the ratio of the spectral power to the maximum spectral power is between 0.4 and 0.6, and the P-wave polarity is unipolar with reversed polarity.

10. The computer-based method according to claim 4, wherein the endovascular device is a central venous catheter coupled to an adapter that includes an electrode in contact with a saline solution column exposed to a tip of the catheter, and the endovascular ECG signal is based on an electrical signal measured by the electrode.

11. The computer-based method according to claim 10, further comprising:
   simultaneously receiving a skin ECG signal with the endovascular ECG signal, associated with a skin ECG lead, including a plurality of waveforms, each waveform having at least a P-wave component;
   processing the skin ECG signal, over the plurality of predetermined time periods, to calculate a skin P-wave amplitude and a skin spectral power for each predetermined time period;
   determining a maximum skin P-wave amplitude from a plurality of skin P-wave amplitudes resulting from processing the skin ECG signal over the plurality of predetermined time periods, and an associated maximum skin spectral power from a plurality of skin spectral powers resulting from processing the skin ECG signal over the plurality of predetermined time periods;

associating the maximum skin P-wave amplitude and the maximum skin spectral power with the predetermined location in or near the heart; and calculating the location of the endovascular device, for each predetermined time period, based on a ratio of the skin P-wave amplitude to the maximum skin P-wave amplitude and a ratio of the skin spectral power to the maximum skin spectral power.

12. The computer-based method according to claim 11, wherein the location of the endovascular device is an upper portion of a superior vena cava if the ratio of the skin P-wave amplitude to the maximum skin P-wave amplitude is between 0.9 and 1.2, the ratio of the skin spectral power to the maximum skin spectral power is between 0.9 and 1.2, and the P wave polarity is unipolar.

13. The computer-based method according to claim 12, wherein the location of the endovascular device is a lower third of the superior vena cava if the ratio of the skin P-wave amplitude to the maximum skin P-wave amplitude is between 1.5 and 2.0, the ratio of the skin spectral power to the maximum skin spectral power is between 1.5 and 2.0, and the P-wave polarity is unipolar.

14. The computer-based method according to claim 13, further comprising: calculating an R-wave amplitude for each predetermined time period when processing the skin ECG signal, wherein the location of the endovascular device is the caval-atrial junction if the ratio of the skin P-wave amplitude to the maximum skin P-wave amplitude is greater than 2.5, the ratio of the skin spectral power to the maximum skin spectral power is greater than 2.59, and the skin P-wave amplitude is greater than the skin R-wave amplitude.

15. The computer-based method according to claim 14, wherein the location of the endovascular device is a right atrium if the ratio of the skin spectral power to the maximum skin spectral power is between 2.0 and 2.5, and a skin P-wave polarity determined for each skin P-wave amplitude for each predetermined time period is bipolar.

16. The computer-based method according to claim 15, wherein the location of the endovascular device is an upper third of an inferior vena cava if the ratio of the skin P-wave amplitude to the maximum skin P-wave amplitude is between 0.9 and 1.2, the ratio of the skin spectral power to the maximum skin spectral power is between 0.9 and 1.2, and the P-wave polarity is unipolar with reversed polarity.

* * * * *